US010220522B2

(12) United States Patent
Rockrohr

(10) Patent No.: US 10,220,522 B2
(45) Date of Patent: Mar. 5, 2019

(54) GEAR TRAIN ASSEMBLIES FOR ROBOTIC SURGICAL SYSTEMS

(71) Applicant: Covidien LP, Mansfield, MA (US)

(72) Inventor: Brian Rockrohr, Waterbury, CT (US)

(73) Assignee: Covidien LP, Mansfield, MA (US)

( * ) Notice: Subject to any disclaimer, the term of this patent is extended or adjusted under 35 U.S.C. 154(b) by 428 days.

(21) Appl. No.: 15/102,908

(22) PCT Filed: Oct. 23, 2014

(86) PCT No.: PCT/US2014/061863
§ 371 (c)(1),
(2) Date: Jun. 9, 2016

(87) PCT Pub. No.: WO2015/088655
PCT Pub. Date: Jun. 18, 2015

(65) Prior Publication Data
US 2016/0303745 A1    Oct. 20, 2016

Related U.S. Application Data

(60) Provisional application No. 61/914,979, filed on Dec. 12, 2013.

(51) Int. Cl.
*A61B 17/29* (2006.01)
*B25J 17/02* (2006.01)
(Continued)

(52) U.S. Cl.
CPC ..... *B25J 17/0258* (2013.01); *A61B 17/00234* (2013.01); *A61B 34/30* (2016.02);
(Continued)

(58) Field of Classification Search
CPC ...... A61B 34/30; A61B 34/71; B25J 15/0213; B25J 17/0258; B25J 9/102
(Continued)

(56) References Cited

U.S. PATENT DOCUMENTS 2,777,340 A    1/1957   Hettwer et al.
2,957,353 A    10/1960  Babacz
(Continued)

FOREIGN PATENT DOCUMENTS

CA    2451558 A1    1/2003
CN    1547454 A     11/2004
(Continued)

OTHER PUBLICATIONS

Chinese Second Office Action corresponding to counterpart Patent Appln. CN 2014800674869 dated Aug. 1, 2018.
(Continued)

*Primary Examiner* — Vy Bui

(57) ABSTRACT

An end effector for use and connection to a robot arm of a robotic surgical system, wherein the end effector is controlled and/or articulated by at least one cable extending from a respective motor of a control device of the robot surgical system, is provided. The end effector includes at least one gear train that transmits forces from the at least one motor of the control device to at least one of the proximal bracket of the wrist assembly, the distal bracket of the wrist assembly and the jaw assembly. The gear train enables at least one of a pivoting of the distal hub assembly relative to the proximal hub; a rotation of the distal bracket relative to the proximal bracket; and an opening/closing of the jaw assembly.

20 Claims, 8 Drawing Sheets

(51) Int. Cl.
  *B25J 9/10*      (2006.01)
  *B25J 15/02*     (2006.01)
  *A61B 34/00*     (2016.01)
  *A61B 34/30*     (2016.01)
  *A61B 17/00*     (2006.01)

(52) U.S. Cl.
  CPC .............. *A61B 34/71* (2016.02); *B25J 9/102* (2013.01); *B25J 15/0213* (2013.01); *A61B 17/29* (2013.01); *A61B 2017/00323* (2013.01); *A61B 2017/2927* (2013.01); *A61B 2017/2929* (2013.01); *A61B 2017/2932* (2013.01); *A61B 2017/2943* (2013.01)

(58) Field of Classification Search
  USPC ................................. 606/1, 34, 51, 130, 169
  See application file for complete search history.

(56) References Cited

U.S. PATENT DOCUMENTS

| | | | |
|---|---|---|---|
| 3,111,328 | A | 11/1963 | Di Rito et al. |
| 3,695,058 | A | 10/1972 | Keith, Jr. |
| 3,734,515 | A | 5/1973 | Dudek |
| 3,759,336 | A | 9/1973 | Marcovitz et al. |
| 4,162,399 | A | 7/1979 | Hudson |
| 4,606,343 | A | 8/1986 | Conta et al. |
| 4,683,772 | A | 8/1987 | Colimitra |
| 4,705,038 | A | 11/1987 | Sjostrom et al. |
| 4,722,685 | A | 2/1988 | de Estrada et al. |
| 4,823,807 | A | 4/1989 | Russell et al. |
| 4,862,759 | A * | 9/1989 | Trevelyan ............... B25J 9/103 74/417 |
| 4,874,181 | A | 10/1989 | Hsu |
| 5,129,118 | A | 7/1992 | Walmesley |
| 5,129,570 | A | 7/1992 | Schulze et al. |
| 5,152,744 | A | 10/1992 | Krause et al. |
| 5,301,061 | A | 4/1994 | Nakada et al. |
| 5,312,023 | A | 5/1994 | Green et al. |
| 5,326,013 | A | 7/1994 | Green et al. |
| 5,350,355 | A | 9/1994 | Sklar |
| 5,383,874 | A | 1/1995 | Jackson et al. |
| 5,383,880 | A | 1/1995 | Hooven |
| 5,389,098 | A | 2/1995 | Tsuruta et al. |
| 5,395,033 | A | 3/1995 | Byrne et al. |
| 5,400,267 | A | 3/1995 | Denen et al. |
| 5,411,508 | A | 5/1995 | Bessler et al. |
| 5,413,267 | A | 5/1995 | Solyntjes et al. |
| 5,427,087 | A | 6/1995 | Ito et al. |
| 5,433,721 | A | 7/1995 | Hooven et al. |
| 5,467,911 | A | 11/1995 | Tsuruta et al. |
| 5,476,379 | A | 12/1995 | Disel |
| 5,487,499 | A | 1/1996 | Sorrentino et al. |
| 5,518,163 | A | 5/1996 | Hooven |
| 5,518,164 | A | 5/1996 | Hooven |
| 5,526,822 | A | 6/1996 | Burbank et al. |
| 5,529,235 | A | 6/1996 | Boiarski et al. |
| 5,535,934 | A | 7/1996 | Boiarski et al. |
| 5,535,937 | A | 7/1996 | Boiarski et al. |
| 5,540,375 | A | 7/1996 | Bolanos et al. |
| 5,540,706 | A | 7/1996 | Aust et al. |
| 5,542,594 | A | 8/1996 | McKean et al. |
| 5,549,637 | A | 8/1996 | Crainich |
| 5,553,675 | A | 9/1996 | Pitzen et al. |
| 5,562,239 | A | 10/1996 | Boiarski et al. |
| 5,564,615 | A | 10/1996 | Bishop et al. |
| 5,609,560 | A | 3/1997 | Ichikawa et al. |
| 5,626,587 | A | 5/1997 | Bishop et al. |
| 5,632,432 | A | 5/1997 | Schulze et al. |
| 5,645,209 | A | 7/1997 | Green et al. |
| 5,647,526 | A | 7/1997 | Green et al. |
| 5,653,374 | A | 8/1997 | Young et al. |
| 5,658,300 | A | 8/1997 | Bito et al. |
| 5,662,662 | A | 9/1997 | Bishop et al. |
| 5,667,517 | A | 9/1997 | Hooven |
| 5,693,042 | A | 12/1997 | Boiarski et al. |
| 5,704,534 | A | 1/1998 | Huitema et al. |
| 5,713,505 | A | 2/1998 | Huitema |
| 5,762,603 | A | 6/1998 | Thompson |
| 5,779,130 | A | 7/1998 | Alesi et al. |
| 5,782,396 | A | 7/1998 | Mastri et al. |
| 5,782,397 | A | 7/1998 | Koukline |
| 5,784,542 | A | 7/1998 | Ohm et al. |
| 5,792,573 | A | 8/1998 | Pitzen et al. |
| 5,797,536 | A | 8/1998 | Smith et al. |
| 5,797,900 | A * | 8/1998 | Madhani ................... B25J 3/04 606/1 |
| 5,820,009 | A | 10/1998 | Melling et al. |
| 5,863,159 | A | 1/1999 | Lasko |
| 5,908,427 | A | 6/1999 | McKean et al. |
| 5,954,259 | A | 9/1999 | Viola et al. |
| 5,964,774 | A | 10/1999 | McKean et al. |
| 5,993,454 | A | 11/1999 | Longo |
| 6,010,054 | A | 1/2000 | Johnson et al. |
| 6,017,354 | A | 1/2000 | Culp et al. |
| 6,032,849 | A | 3/2000 | Mastri et al. |
| 6,045,560 | A | 4/2000 | McKean et al. |
| 6,090,123 | A | 7/2000 | Culp et al. |
| 6,126,651 | A | 10/2000 | Mayer |
| 6,129,547 | A | 10/2000 | Cise et al. |
| 6,165,169 | A | 12/2000 | Panescu et al. |
| 6,239,732 | B1 | 5/2001 | Cusey |
| 6,241,139 | B1 | 6/2001 | Milliman et al. |
| 6,264,086 | B1 | 7/2001 | McGuckin, Jr. |
| 6,264,087 | B1 | 7/2001 | Whitman |
| 6,302,311 | B1 | 10/2001 | Adams et al. |
| 6,315,184 | B1 | 11/2001 | Whitman |
| 6,321,855 | B1 | 11/2001 | Barnes |
| 6,329,778 | B1 | 12/2001 | Culp et al. |
| 6,343,731 | B1 | 2/2002 | Adams et al. |
| 6,348,061 | B1 | 2/2002 | Whitman |
| 6,368,324 | B1 | 4/2002 | Dinger et al. |
| 6,371,909 | B1 | 4/2002 | Hoeg et al. |
| 6,434,507 | B1 | 8/2002 | Clayton et al. |
| 6,443,973 | B1 | 9/2002 | Whitman |
| 6,461,372 | B1 | 10/2002 | Jensen et al. |
| 6,488,197 | B1 | 12/2002 | Whitman |
| 6,491,201 | B1 | 12/2002 | Whitman |
| 6,533,157 | B1 | 3/2003 | Whitman |
| 6,537,280 | B2 | 3/2003 | Dinger et al. |
| 6,554,844 | B2 | 4/2003 | Lee et al. |
| 6,610,066 | B2 | 8/2003 | Dinger et al. |
| 6,611,793 | B1 | 8/2003 | Burnside et al. |
| 6,645,218 | B1 | 11/2003 | Cassidy et al. |
| 6,654,999 | B2 | 12/2003 | Stoddard et al. |
| 6,698,643 | B2 | 3/2004 | Whitman |
| 6,699,177 | B1 | 3/2004 | Wang et al. |
| 6,716,233 | B1 | 4/2004 | Whitman |
| 6,743,240 | B2 | 6/2004 | Smith et al. |
| 6,783,533 | B2 | 8/2004 | Green et al. |
| 6,792,390 | B1 | 9/2004 | Burnside et al. |
| 6,793,652 | B1 | 9/2004 | Whitman et al. |
| 6,817,508 | B1 | 11/2004 | Racenet et al. |
| 6,830,174 | B2 | 12/2004 | Hillstead et al. |
| 6,846,308 | B2 | 1/2005 | Whitman et al. |
| 6,846,309 | B2 | 1/2005 | Whitman et al. |
| 6,849,071 | B2 | 2/2005 | Whitman et al. |
| 6,860,892 | B1 | 3/2005 | Tanaka et al. |
| 6,899,538 | B2 | 5/2005 | Matoba |
| 6,905,057 | B2 | 6/2005 | Swayze et al. |
| 6,959,852 | B2 | 11/2005 | Shelton, IV et al. |
| 6,964,363 | B2 | 11/2005 | Wales et al. |
| 6,981,628 | B2 | 1/2006 | Wales |
| 6,981,941 | B2 | 1/2006 | Whitman et al. |
| 6,986,451 | B1 | 1/2006 | Mastri et al. |
| 6,988,649 | B2 | 1/2006 | Shelton, IV et al. |
| 7,032,798 | B2 | 4/2006 | Whitman et al. |
| RE39,152 | E | 6/2006 | Aust et al. |
| 7,055,731 | B2 | 6/2006 | Shelton, IV et al. |
| 7,059,508 | B2 | 6/2006 | Shelton, IV et al. |
| 7,077,856 | B2 | 7/2006 | Whitman |
| 7,111,769 | B2 | 9/2006 | Wales et al. |
| 7,122,029 | B2 | 10/2006 | Koop et al. |
| 7,140,528 | B2 | 11/2006 | Shelton, IV |

(56) References Cited

U.S. PATENT DOCUMENTS

| | | |
|---|---|---|
| 7,141,049 B2 | 11/2006 | Stern et al. |
| 7,143,923 B2 | 12/2006 | Shelton, IV et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,172,104 B2 | 2/2007 | Scirica et al. |
| 7,225,964 B2 | 6/2007 | Mastri et al. |
| 7,238,021 B1 | 7/2007 | Johnson |
| 7,246,734 B2 | 7/2007 | Shelton, IV |
| 7,252,660 B2 | 8/2007 | Kunz |
| 7,328,828 B2 | 2/2008 | Ortiz et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,422,139 B2 | 9/2008 | Shelton, IV et al. |
| 7,422,592 B2 * | 9/2008 | Morley ............... A61B 18/1445 606/49 |
| 7,431,189 B2 | 10/2008 | Shelton, IV et al. |
| 7,441,684 B2 | 10/2008 | Shelton, IV et al. |
| 7,448,525 B2 | 11/2008 | Shelton, IV et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,347 B2 | 1/2009 | Roy |
| 7,481,824 B2 | 1/2009 | Boudreaux et al. |
| 7,487,899 B2 | 2/2009 | Shelton, IV et al. |
| 7,549,564 B2 | 6/2009 | Boudreaux |
| 7,565,993 B2 | 7/2009 | Milliman et al. |
| 7,568,603 B2 | 8/2009 | Shelton, IV et al. |
| 7,575,144 B2 | 8/2009 | Ortiz et al. |
| 7,588,175 B2 | 9/2009 | Timm et al. |
| 7,588,176 B2 | 9/2009 | Timm et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,670,334 B2 | 3/2010 | Hueil et al. |
| 7,673,780 B2 | 3/2010 | Shelton, IV et al. |
| 7,699,835 B2 | 4/2010 | Lee et al. |
| 7,721,931 B2 | 5/2010 | Shelton, IV et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,758,613 B2 | 7/2010 | Whitman |
| 7,766,210 B2 | 8/2010 | Shelton, IV et al. |
| 7,770,773 B2 | 8/2010 | Whitman et al. |
| 7,770,775 B2 | 8/2010 | Shelton, IV et al. |
| 7,793,812 B2 | 9/2010 | Moore et al. |
| 7,799,039 B2 | 9/2010 | Shelton, IV et al. |
| 7,802,712 B2 | 9/2010 | Milliman et al. |
| 7,803,151 B2 | 9/2010 | Whitman |
| 7,822,458 B2 | 10/2010 | Webster, III et al. |
| 7,845,534 B2 | 12/2010 | Viola et al. |
| 7,845,537 B2 | 12/2010 | Shelton, IV et al. |
| 7,857,185 B2 | 12/2010 | Swayze et al. |
| 7,870,989 B2 | 1/2011 | Viola et al. |
| 7,900,805 B2 | 3/2011 | Shelton, IV et al. |
| 7,905,897 B2 | 3/2011 | Whitman et al. |
| 7,918,230 B2 | 4/2011 | Whitman et al. |
| 7,922,061 B2 | 4/2011 | Shelton, IV et al. |
| 7,922,719 B2 | 4/2011 | Ralph et al. |
| 7,947,034 B2 | 5/2011 | Whitman |
| 7,951,071 B2 | 5/2011 | Whitman et al. |
| 7,954,682 B2 | 6/2011 | Giordano et al. |
| 7,959,051 B2 | 6/2011 | Smith et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,992,758 B2 | 8/2011 | Whitman et al. |
| 8,011,550 B2 | 9/2011 | Aranyi et al. |
| 8,016,178 B2 | 9/2011 | Olson et al. |
| 8,016,855 B2 | 9/2011 | Whitman et al. |
| 8,020,743 B2 | 9/2011 | Shelton, IV |
| 8,025,199 B2 | 9/2011 | Whitman et al. |
| 8,035,487 B2 | 10/2011 | Malackowski |
| 8,052,024 B2 | 11/2011 | Viola et al. |
| 8,074,859 B2 | 12/2011 | Kostrzewski |
| 8,092,451 B2 | 1/2012 | Schechter et al. |
| 8,114,118 B2 | 2/2012 | Knodel et al. |
| 8,127,975 B2 | 3/2012 | Olson et al. |
| 8,132,705 B2 | 3/2012 | Viola et al. |
| 8,152,516 B2 | 4/2012 | Harvey et al. |
| 8,157,150 B2 | 4/2012 | Viola et al. |
| 8,157,151 B2 | 4/2012 | Ingmanson et al. |
| 8,182,494 B1 | 5/2012 | Yencho et al. |
| 8,186,555 B2 | 5/2012 | Shelton, IV et al. |
| 8,186,587 B2 | 5/2012 | Zmood et al. |
| 8,220,367 B2 | 7/2012 | Hsu |
| 8,235,273 B2 | 8/2012 | Olson et al. |
| 8,237,388 B2 | 8/2012 | Jinno et al. |
| 8,241,322 B2 | 8/2012 | Whitman et al. |
| 8,272,554 B2 | 9/2012 | Whitman et al. |
| 8,292,150 B2 | 10/2012 | Bryant |
| 8,292,888 B2 | 10/2012 | Whitman |
| 8,342,379 B2 | 1/2013 | Whitman et al. |
| 8,348,130 B2 | 1/2013 | Shah et al. |
| 8,348,855 B2 | 1/2013 | Hillely et al. |
| 8,353,440 B2 | 1/2013 | Whitman et al. |
| 8,357,144 B2 | 1/2013 | Whitman et al. |
| 8,365,633 B2 | 2/2013 | Simaan et al. |
| 8,365,972 B2 | 2/2013 | Aranyi et al. |
| 8,371,492 B2 | 2/2013 | Aranyi et al. |
| 8,372,057 B2 | 2/2013 | Cude et al. |
| 8,391,957 B2 | 3/2013 | Carlson et al. |
| 8,403,926 B2 | 3/2013 | Nobis et al. |
| 8,418,904 B2 | 4/2013 | Wenchell et al. |
| 8,424,739 B2 | 4/2013 | Racenet et al. |
| 8,454,585 B2 | 6/2013 | Whitman |
| 8,505,802 B2 | 8/2013 | Viola et al. |
| 8,517,241 B2 | 8/2013 | Nicholas et al. |
| 8,523,043 B2 | 9/2013 | Ullrich et al. |
| 8,551,076 B2 | 10/2013 | Duval et al. |
| 8,561,871 B2 | 10/2013 | Rajappa et al. |
| 8,561,874 B2 | 10/2013 | Scirica |
| 8,602,287 B2 | 12/2013 | Yates et al. |
| 8,623,000 B2 | 1/2014 | Humayun et al. |
| 8,627,995 B2 | 1/2014 | Smith et al. |
| 8,632,463 B2 | 1/2014 | Drinan et al. |
| 8,636,766 B2 | 1/2014 | Milliman et al. |
| 8,647,258 B2 | 2/2014 | Aranyi et al. |
| 8,652,121 B2 | 2/2014 | Quick et al. |
| 8,657,174 B2 | 2/2014 | Yates et al. |
| 8,657,177 B2 | 2/2014 | Scirica et al. |
| 8,672,206 B2 | 3/2014 | Aranyi et al. |
| 8,696,552 B2 | 4/2014 | Whitman |
| 8,708,213 B2 | 4/2014 | Shelton, IV et al. |
| 8,715,306 B2 | 5/2014 | Faller et al. |
| 8,758,391 B2 | 6/2014 | Swayze et al. |
| 8,806,973 B2 | 8/2014 | Ross et al. |
| 8,808,311 B2 | 8/2014 | Heinrich et al. |
| 8,820,605 B2 | 9/2014 | Shelton, IV |
| 8,851,355 B2 | 10/2014 | Aranyi et al. |
| 8,858,571 B2 | 10/2014 | Shelton, IV et al. |
| 8,875,972 B2 | 11/2014 | Weisenburgh, II et al. |
| 8,888,762 B2 | 11/2014 | Whitman |
| 8,893,946 B2 | 11/2014 | Boudreaux et al. |
| 8,899,462 B2 | 12/2014 | Kostrzewski et al. |
| 8,905,289 B2 | 12/2014 | Patel et al. |
| 8,919,630 B2 | 12/2014 | Milliman |
| 8,931,680 B2 | 1/2015 | Milliman |
| 8,939,344 B2 | 1/2015 | Olson et al. |
| 8,950,646 B2 | 2/2015 | Viola |
| 8,960,519 B2 | 2/2015 | Whitman et al. |
| 8,961,396 B2 | 2/2015 | Azarbarzin et al. |
| 8,967,443 B2 | 3/2015 | McCuen |
| 8,968,276 B2 | 3/2015 | Zemlok et al. |
| 8,968,337 B2 | 3/2015 | Whitfield et al. |
| 8,992,422 B2 | 3/2015 | Spivey et al. |
| 9,016,545 B2 | 4/2015 | Aranyi et al. |
| 9,023,014 B2 | 5/2015 | Chowaniec et al. |
| 9,033,868 B2 | 5/2015 | Whitman et al. |

(56) References Cited

U.S. PATENT DOCUMENTS

| | | |
|---|---|---|
| 9,055,943 B2 | 6/2015 | Zemlok et al. |
| 9,064,653 B2 | 6/2015 | Prest et al. |
| 9,072,515 B2 | 7/2015 | Hall et al. |
| 9,113,847 B2 | 8/2015 | Whitman et al. |
| 9,113,875 B2 | 8/2015 | Viola et al. |
| 9,113,876 B2 | 8/2015 | Zemlok et al. |
| 9,113,899 B2 | 8/2015 | Garrison et al. |
| 9,216,013 B2 | 12/2015 | Scirica et al. |
| 9,241,712 B2 | 1/2016 | Zemlok et al. |
| 9,282,961 B2 | 3/2016 | Whitman et al. |
| 9,282,963 B2 | 3/2016 | Bryant |
| 9,295,522 B2 | 3/2016 | Kostrzewski |
| 9,307,986 B2 | 4/2016 | Hall et al. |
| 2001/0031975 A1 | 10/2001 | Whitman et al. |
| 2002/0040217 A1 | 4/2002 | Jinno |
| 2002/0049454 A1 | 4/2002 | Whitman et al. |
| 2002/0165541 A1 | 11/2002 | Whitman |
| 2003/0038938 A1 | 2/2003 | Jung et al. |
| 2003/0165794 A1 | 9/2003 | Matoba |
| 2004/0034369 A1 | 2/2004 | Sauer et al. |
| 2004/0111012 A1 | 6/2004 | Whitman |
| 2004/0133189 A1 | 7/2004 | Sakurai |
| 2004/0153124 A1 | 8/2004 | Whitman |
| 2004/0176751 A1 | 9/2004 | Weitzner et al. |
| 2004/0193146 A1 | 9/2004 | Lee et al. |
| 2005/0125027 A1 | 6/2005 | Knodel et al. |
| 2005/0131442 A1 | 6/2005 | Yachia et al. |
| 2006/0142656 A1 | 6/2006 | Malackowski et al. |
| 2006/0142740 A1 | 6/2006 | Sherman et al. |
| 2006/0142744 A1 | 6/2006 | Boutoussov |
| 2006/0259073 A1 | 11/2006 | Miyamoto et al. |
| 2006/0278680 A1 | 12/2006 | Viola et al. |
| 2006/0284730 A1 | 12/2006 | Schmid et al. |
| 2007/0023476 A1 | 2/2007 | Whitman et al. |
| 2007/0023477 A1 | 2/2007 | Whitman et al. |
| 2007/0029363 A1 | 2/2007 | Popov |
| 2007/0084897 A1 | 4/2007 | Shelton et al. |
| 2007/0102472 A1 | 5/2007 | Shelton |
| 2007/0152014 A1 | 7/2007 | Gillum et al. |
| 2007/0175947 A1 | 8/2007 | Ortiz et al. |
| 2007/0175949 A1 | 8/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0175961 A1 | 8/2007 | Shelton et al. |
| 2007/0270784 A1 | 11/2007 | Smith et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0039256 A1 | 2/2008 | Jinno et al. |
| 2008/0058801 A1 | 3/2008 | Taylor et al. |
| 2008/0109012 A1 | 5/2008 | Falco et al. |
| 2008/0110958 A1 | 5/2008 | McKenna et al. |
| 2008/0147089 A1 | 6/2008 | Loh et al. |
| 2008/0167736 A1 | 7/2008 | Swayze et al. |
| 2008/0185419 A1 | 8/2008 | Smith et al. |
| 2008/0188841 A1 | 8/2008 | Tomasello et al. |
| 2008/0197167 A1 | 8/2008 | Viola et al. |
| 2008/0208195 A1 | 8/2008 | Shores et al. |
| 2008/0237296 A1 | 10/2008 | Boudreaux et al. |
| 2008/0245175 A1 | 10/2008 | Jinno et al. |
| 2008/0251561 A1 | 10/2008 | Eades et al. |
| 2008/0255413 A1 | 10/2008 | Zemlok et al. |
| 2008/0255607 A1 | 10/2008 | Zemlok |
| 2008/0262654 A1 | 10/2008 | Omori et al. |
| 2008/0308603 A1 | 12/2008 | Shelton et al. |
| 2009/0012533 A1 | 1/2009 | Barbagli et al. |
| 2009/0090763 A1 | 4/2009 | Zemlok et al. |
| 2009/0099876 A1 | 4/2009 | Whitman |
| 2009/0138006 A1 | 5/2009 | Bales et al. |
| 2009/0171147 A1 | 7/2009 | Lee et al. |
| 2009/0182193 A1 | 7/2009 | Whitman et al. |
| 2009/0209946 A1 | 8/2009 | Swayze et al. |
| 2009/0209990 A1 | 8/2009 | Yates et al. |
| 2009/0254094 A1 | 10/2009 | Knapp et al. |
| 2009/0299141 A1 | 12/2009 | Downey et al. |
| 2010/0016852 A1 | 1/2010 | Manzo et al. |
| 2010/0016853 A1 | 1/2010 | Burbank |
| 2010/0023022 A1 | 1/2010 | Zeiner et al. |
| 2010/0069942 A1 | 3/2010 | Shelton, IV |
| 2010/0193568 A1 | 8/2010 | Scheib et al. |
| 2010/0211053 A1 | 8/2010 | Ross et al. |
| 2010/0225073 A1 | 9/2010 | Porter et al. |
| 2011/0071508 A1 | 3/2011 | Duval et al. |
| 2011/0077673 A1 | 3/2011 | Grubac et al. |
| 2011/0121049 A1 | 5/2011 | Malinouskas et al. |
| 2011/0125138 A1 | 5/2011 | Malinouskas et al. |
| 2011/0139851 A1 | 6/2011 | McCuen |
| 2011/0155783 A1 | 6/2011 | Rajappa et al. |
| 2011/0155786 A1 | 6/2011 | Shelton, IV |
| 2011/0172648 A1 | 7/2011 | Jeong |
| 2011/0174009 A1 | 7/2011 | Iizuka et al. |
| 2011/0174099 A1 | 7/2011 | Ross et al. |
| 2011/0184245 A1 | 7/2011 | Xia et al. |
| 2011/0204119 A1 | 8/2011 | McCuen |
| 2011/0218522 A1 | 9/2011 | Whitman |
| 2011/0276057 A1 | 11/2011 | Conlon et al. |
| 2011/0290854 A1 | 12/2011 | Timm et al. |
| 2011/0295242 A1 | 12/2011 | Spivey et al. |
| 2011/0295269 A1 | 12/2011 | Swensgard et al. |
| 2012/0000962 A1 | 1/2012 | Racenet et al. |
| 2012/0010616 A1 | 1/2012 | Huang et al. |
| 2012/0074199 A1 | 3/2012 | Olson et al. |
| 2012/0080475 A1 | 4/2012 | Smith et al. |
| 2012/0080485 A1 | 4/2012 | Woodard, Jr. et al. |
| 2012/0089131 A1 | 4/2012 | Zemlok et al. |
| 2012/0104071 A1 | 5/2012 | Bryant |
| 2012/0116368 A1 | 5/2012 | Viola |
| 2012/0116416 A1 | 5/2012 | Neff et al. |
| 2012/0143002 A1 | 6/2012 | Aranyi et al. |
| 2012/0168485 A1 | 7/2012 | Marczyk et al. |
| 2012/0172924 A1 | 7/2012 | Allen, IV |
| 2012/0199630 A1 | 8/2012 | Shelton |
| 2012/0211542 A1 | 8/2012 | Racenet |
| 2012/0223121 A1 | 9/2012 | Viola et al. |
| 2012/0245428 A1 | 9/2012 | Smith et al. |
| 2012/0253329 A1 | 10/2012 | Zemlok et al. |
| 2012/0310220 A1 | 12/2012 | Malkowski et al. |
| 2012/0323226 A1 | 12/2012 | Chowaniec et al. |
| 2012/0330285 A1 | 12/2012 | Hartoumbekis et al. |
| 2013/0020376 A1 | 1/2013 | Shelton, IV et al. |
| 2013/0032629 A1 | 2/2013 | Viola |
| 2013/0093149 A1 | 4/2013 | Saur et al. |
| 2013/0131695 A1 | 5/2013 | Scarfogliero et al. |
| 2013/0158542 A1 | 6/2013 | Manzo et al. |
| 2013/0181035 A1 | 7/2013 | Milliman |
| 2013/0184704 A1 | 7/2013 | Beardsley et al. |
| 2013/0214025 A1 | 8/2013 | Zemlok et al. |
| 2013/0274722 A1 | 10/2013 | Kostrzewski et al. |
| 2013/0282052 A1 | 10/2013 | Aranyi et al. |
| 2013/0292451 A1 | 11/2013 | Viola et al. |
| 2013/0313304 A1 | 11/2013 | Shelton, IV et al. |
| 2013/0317486 A1 | 11/2013 | Nicholas et al. |
| 2013/0319706 A1 | 12/2013 | Nicholas et al. |
| 2013/0324978 A1 | 12/2013 | Nicholas et al. |
| 2013/0324979 A1 | 12/2013 | Nicholas et al. |
| 2013/0334281 A1 | 12/2013 | Williams |
| 2014/0012236 A1 | 1/2014 | Williams et al. |
| 2014/0012237 A1 | 1/2014 | Pribanic et al. |
| 2014/0012289 A1 | 1/2014 | Snow et al. |
| 2014/0025046 A1 | 1/2014 | Williams et al. |
| 2014/0110455 A1 | 4/2014 | Ingmanson et al. |
| 2014/0207125 A1 | 7/2014 | Applegate et al. |
| 2014/0207182 A1 | 7/2014 | Zergiebel et al. |
| 2014/0207185 A1 | 7/2014 | Goble et al. |
| 2014/0236174 A1 | 8/2014 | Williams et al. |
| 2014/0276932 A1 | 9/2014 | Williams et al. |
| 2014/0299647 A1 | 10/2014 | Scirica et al. |
| 2014/0303668 A1 | 10/2014 | Nicholas et al. |
| 2014/0358129 A1 | 12/2014 | Zergiebel et al. |
| 2014/0361068 A1 | 12/2014 | Aranyi et al. |
| 2014/0365235 A1 | 12/2014 | DeBoer et al. |
| 2014/0373652 A1 | 12/2014 | Zergiebel et al. |

(56) References Cited

U.S. PATENT DOCUMENTS

| | | |
|---|---|---|
| 2015/0014392 A1 | 1/2015 | Williams et al. |
| 2015/0048144 A1 | 2/2015 | Whitman |
| 2015/0076205 A1 | 3/2015 | Zergiebel |
| 2015/0080912 A1 | 3/2015 | Sapre |
| 2015/0112381 A1 | 4/2015 | Richard |
| 2015/0122870 A1 | 5/2015 | Zemlok et al. |
| 2015/0133224 A1 | 5/2015 | Whitman et al. |
| 2015/0150547 A1 | 6/2015 | Ingmanson et al. |
| 2015/0150574 A1 | 6/2015 | Richard et al. |
| 2015/0157320 A1 | 6/2015 | Zergiebel et al. |
| 2015/0157321 A1 | 6/2015 | Zergiebel et al. |
| 2015/0164502 A1 | 6/2015 | Richard et al. |
| 2015/0201931 A1 | 7/2015 | Zergiebel et al. |
| 2015/0272577 A1 | 10/2015 | Zemlok et al. |
| 2015/0297199 A1 | 10/2015 | Nicholas et al. |
| 2015/0303996 A1 | 10/2015 | Calderoni |
| 2015/0320420 A1 | 11/2015 | Penna et al. |
| 2015/0327850 A1 | 11/2015 | Kostrzewski |
| 2015/0342601 A1 | 12/2015 | Williams et al. |
| 2015/0342603 A1 | 12/2015 | Zergiebel et al. |
| 2015/0374366 A1 | 12/2015 | Zergiebel et al. |
| 2015/0374370 A1 | 12/2015 | Zergiebel et al. |
| 2015/0374371 A1 | 12/2015 | Richard et al. |
| 2015/0374372 A1 | 12/2015 | Zergiebel et al. |
| 2015/0374449 A1 | 12/2015 | Chowaniec et al. |
| 2015/0380187 A1 | 12/2015 | Zergiebel et al. |
| 2016/0095585 A1 | 4/2016 | Zergiebel et al. |
| 2016/0095596 A1 | 4/2016 | Scirica et al. |
| 2016/0106406 A1 | 4/2016 | Cabrera et al. |
| 2016/0113648 A1 | 4/2016 | Zergiebel et al. |
| 2016/0113649 A1 | 4/2016 | Zergiebel et al. |

FOREIGN PATENT DOCUMENTS

| | | |
|---|---|---|
| CN | 1957854 A | 5/2007 |
| CN | 101495046 A | 7/2009 |
| CN | 102247182 A | 11/2011 |
| DE | 102008053842 A1 | 5/2010 |
| EP | 0443576 A1 | 8/1991 |
| EP | 0705571 A1 | 4/1996 |
| EP | 1563793 A1 | 8/2005 |
| EP | 1769754 A1 | 4/2007 |
| EP | 2316345 A1 | 5/2011 |
| EP | 2668910 A2 | 12/2013 |
| ES | 2333509 A1 | 2/2010 |
| JP | 2005-125075 A | 5/2005 |
| KR | 20120022521 A | 3/2012 |
| WO | 2011/108840 A2 | 9/2011 |
| WO | 2012/040984 A1 | 4/2012 |

OTHER PUBLICATIONS

Extended European Search Report corresponding to counterpart International Application No. EP 14 18 4882.0 dated May 12, 2015.
Canadian Office Action corresponding to counterpart International Application No. CA 2640399 dated May 7, 2015.
Japanese Office Action corresponding to counterpart International Application No. JP 2011-197365 dated Mar. 23, 2015.
Japanese Office Action corresponding to counterpart International Application No. JP 2011-084092 dated May 20, 2015.
Japanese Office Action corresponding to counterpart International Application No. JP 2014-148482 dated Jun. 2, 2015.
Extended European Search Report corresponding to counterpart International Application No. EP 14 18 9358.6 dated Jul. 8, 2015.
Extended European Search Report corresponding to counterpart International Application No. EP 14 19 6148.2 dated Apr. 23, 2015.
Partial European Search Report corresponding to counterpart International Application No. EP 14 19 6704.2 dated May 11,2015.
Australian Office Action corresponding to counterpart International Application No. AU 2010241367 dated Aug. 20, 2015.
Partial European Search Report corresponding to counterpart International Application No. EP 14 19 9783.3 dated Sep. 3, 2015.
Extended European Search Report corresponding to counterpart International Application No. EP 15 16 9962.6 dated Sep. 14, 2015.
Extended European Search Report corresponding to International Application No. EP 15 15 1076.5 dated Apr. 22, 2015.
Japanese Office Action corresponding to International Application No. JP 2011-084092 dated Jan. 14, 2016.
Extended European Search Report corresponding to International Application No. EP 12 19 7970.2 dated Jan. 28, 2016.
Chinese Office Action corresponding to International Application No. CN 201210560638.1 dated Oct. 21, 2015.
European Office Action corresponding to International Application No. EP 14 15 9056.2 dated Oct. 26, 2015.
Australian Examination Report No. 1 corresponding to International Application No. AU 2015200153 dated Dec. 11, 2015.
Australian Examination Report No. 1 corresponding to International Application No. AU 2014204542 dated Jan. 7, 2016.
Chinese Office Action corresponding to International Application No. CN 201310125449.6 dated Feb. 3, 2016.
Extended European Search Report corresponding to International Application No. EP 15 19 0245.9 dated Jan. 28, 2016.
Extended European Search Report corresponding to International Application No. EP 15 16 7793.7 dated Apr. 5, 2016.
European Office Action corresponding to International Application No. EP 14 18 4882.0 dated Apr. 25, 2016.
Extended European Search Report corresponding to International Application No. EP 14 19 6704.2 dated Sep. 24, 2015.
International Search Report and Written Opinion corresponding to Intl Appln. No. PCT/US2015/051837, dated Dec. 21, 2015.
Extended European Search Report corresponding to International Application No. EP 14 19 7563.1 dated Aug. 5, 2015.
Partial European Search Report corresponding to International Application No. EP 15 19 0643.5 dated Feb. 26, 2016.
Extended European Search Report corresponding to International Application No. EP 15 16 6899.3 dated Feb. 3, 2016.
Extended European Search Report corresponding to International Application No. EP 14 19 9783.3 dated Dec. 22, 2015.
Extended European Search Report corresponding to International Application No. EP 15 17 3807.7 dated Nov. 24, 2015.
Extended European Search Report corresponding to International Application No. EP 15 19 0760.7 dated Apr. 1, 2016.
Extended European Search Report corresponding to International Application No. EP 15 17 3803.6 dated Nov. 24, 2015.
Extended European Search Report corresponding to International Application No. EP 15 17 3804.4 dated Nov. 24, 2015.
Extended European Search Report corresponding to International Application No. EP 15 18 8539.9 dated Feb. 17, 2016.
Extended European Search Report corresponding to International Application No. EP 15 17 3910.9 dated Nov. 13, 2015.
European Office Action corresponding to International Application No. EP 14 15 2236.7 dated Aug. 11, 2015.
Extended European Search Report corresponding to International Application No. EP 15 18 4915.5 dated Jan. 5, 2016.
Chinese Office Action corresponding to counterpart Int'l Appln. No. CN 201310369318.2 dated Jun. 28, 2016.
Chinese Office Action (with English translation), dated Jul. 4, 2016, corresponding to Chinese Patent Application No. 2015101559718; 23 total pages.
European Search Report EP 15 156 035.6 dated Aug. 10, 2016.
International Search Report for (PCT/US2014/061863) date of completion is Jan. 21, 2015 (4 pages).
Chinese First Office Action corresponding to counterpart Chinese Patent Appln. No. CN 2014800674869 dated Jan. 24, 2018.
Extended European Search Report corresponding to counterpart EP Application No. 14 87 0110.5 dated Mar. 20, 2018.

* cited by examiner

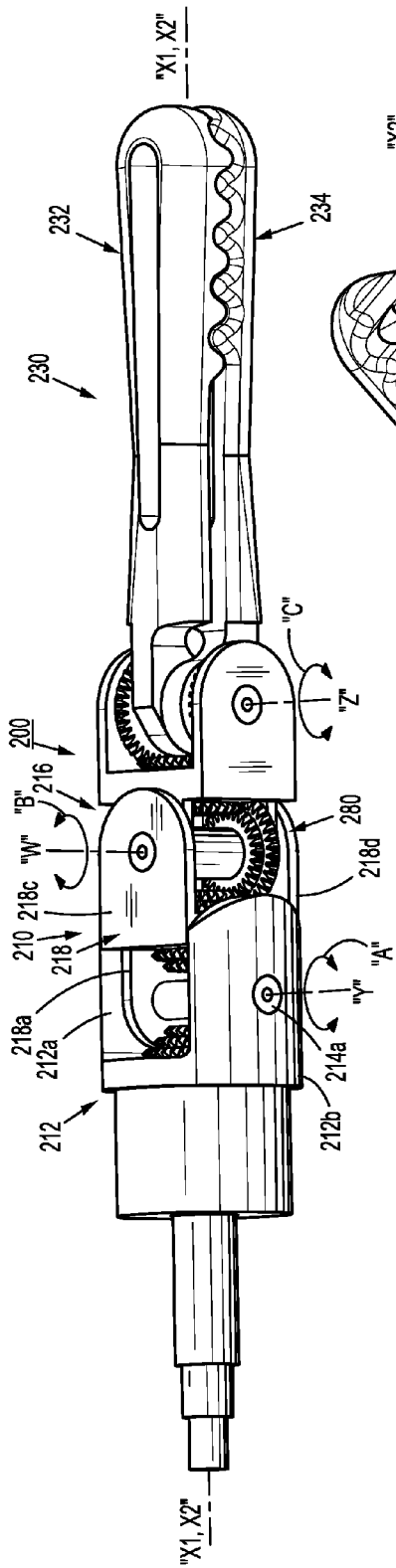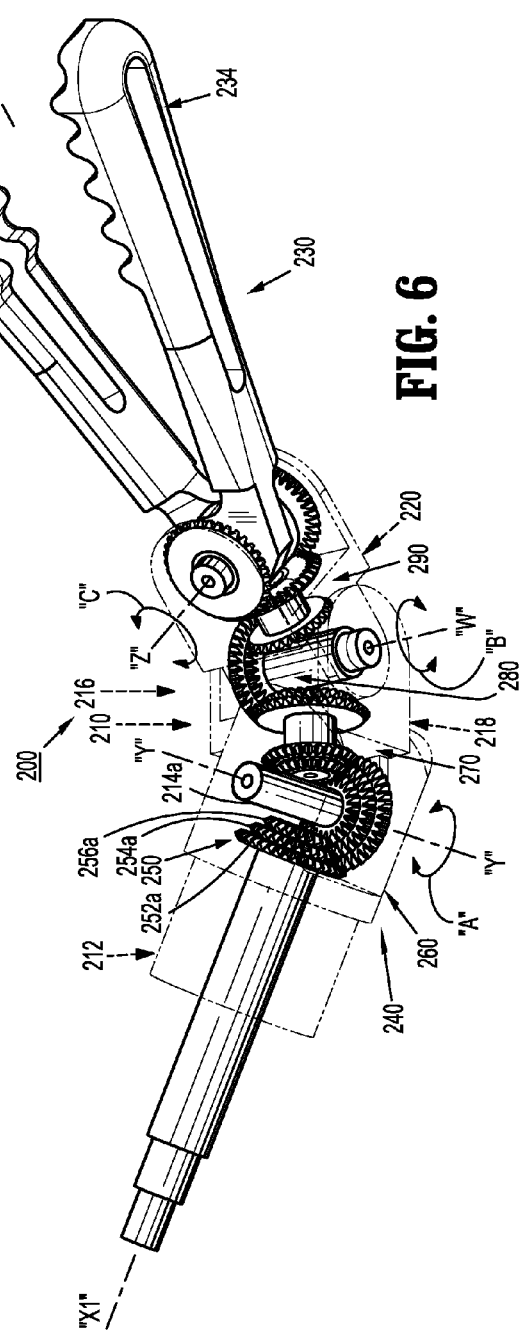

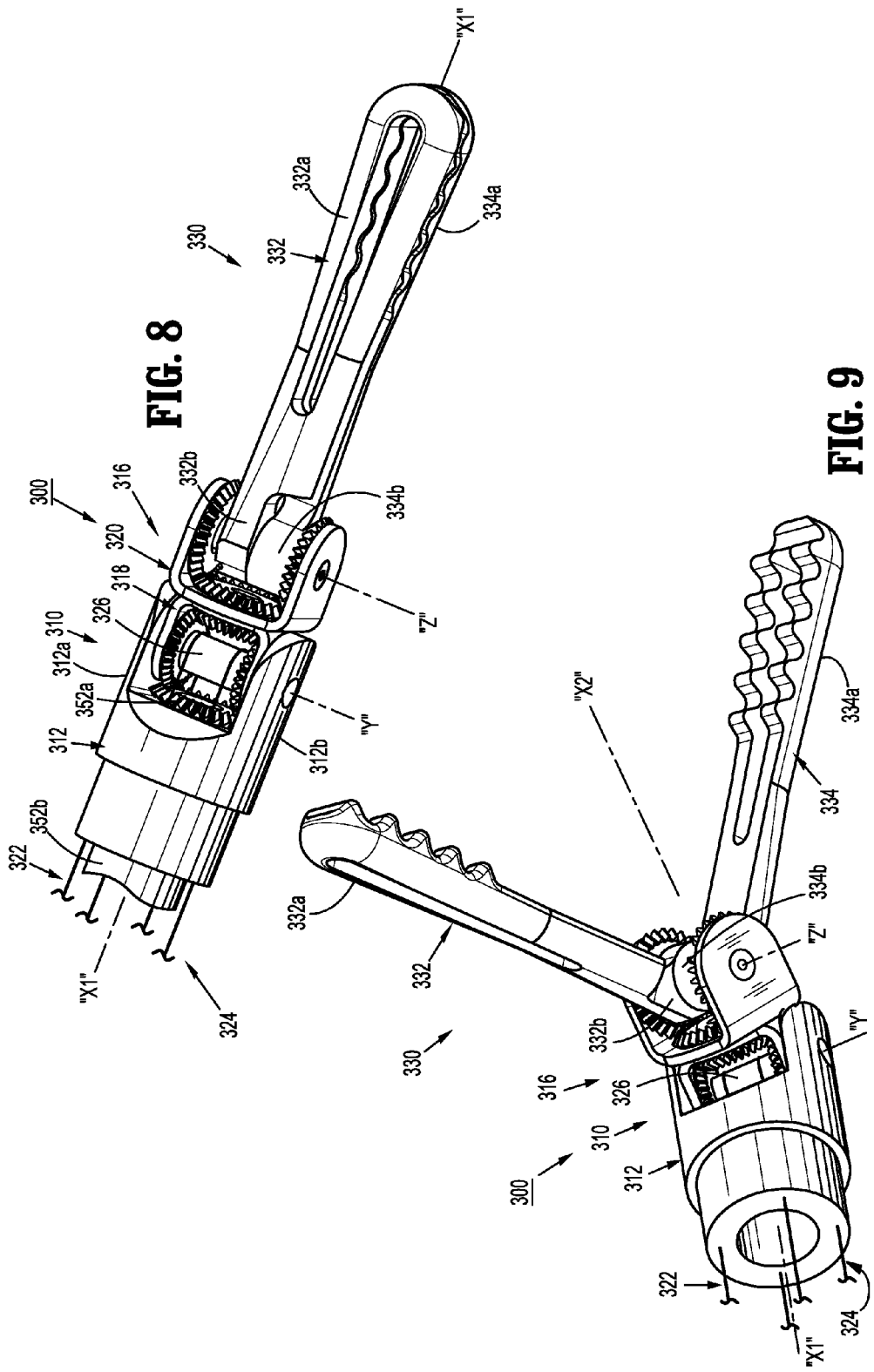

GEAR TRAIN ASSEMBLIES FOR ROBOTIC SURGICAL SYSTEMS

CROSS-REFERENCE TO RELATED APPLICATIONS

This application is a U.S. National Stage application filed under 35 U.S.C. § 371(a) of International Patent Application No. PCT/US2014/061863, filed Oct. 23, 2014, which claims the benefit to U.S. Provisional Patent Application No. 61/914,979, filed Dec. 12, 2013, the entire disclosure of each of which is incorporated by reference herein.

BACKGROUND

Robotic surgical systems have been used in minimally invasive medical procedures. Some robotic surgical systems included a console supporting a robot arm, and at least one end effector such as forceps or a grasping tool that is mounted to the robot arm via a wrist assembly. During a medical procedure, the end effector and the wrist assembly were inserted into a small incision (via a cannula) or a natural orifice of a patient to position the end effector at a work site within the body of the patient.

Cables were extended from the robot console, through the robot arm, and connected to the wrist assembly and/or end effector. In some instances, the cables were actuated by means of motors that were controlled by a processing system including a user interface for a surgeon or clinician to be able to control the robotic surgical system including the robot arm, the wrist assembly and/or the end effector.

In some instances, the wrist assembly provided three degrees of freedom for movement of the end effector through the use of three cables or cable pairs, one for each degree of freedom. For example, for grasping or cutting end effectors the wrist assembly provided the three degrees of freedom by allowing changes to a pitch, a yaw, and an opening and closing of the end effector.

As demand for smaller surgical tools increased, device manufacturers developed surgical tools such as grasping and cutting tools having smaller cross-sectional areas. These smaller cross-sectional areas reduced the total force that could be applied between two jaws at the end of the tools. Additionally, the use of three cables or cable pairs to provide three degrees of motion required a minimum cross-sectional area to implement and limit the ability to further reduce the cross sectional area of these tools. Finally, the force that was applied was not customizable to provide varying forces depending on the position of the jaws in relation to each other as the jaws are opened and closed.

There is a need for surgical tools having relatively small cross-sectional areas and relatively shorter lengths that are able to provide high forces between end effector jaws, including customizable forces that vary depending on the position of the jaws in relation to each other.

SUMMARY

Jaws at the end of surgical robotics tools, such as forceps or scissor cutting tools, may be driven by a cable/tube and gear system. In some instances, the cable/tube and gear system may be driven directly so at least one cable/tube controls a pitch, at least one cable/tube controls a yaw, and at least one cable/tube opens and closes the jaws.

End effectors, including wrist assemblies and jaw assemblies, may be used with and actuated by robotic surgical systems. In some instances, an end effector may be controlled and/or articulated by at least one cable/tube extending from a respective motor of a control device of the robot surgical system.

According to one aspect of the present disclosure, an end effector for use and connection to a robot arm of a robotic surgical system is provided, wherein the end effector is controlled and/or articulated by at least one motor of a control device of the robot surgical system. The end effector comprises a wrist assembly including a proximal hub defining a respective longitudinal axis; and a distal hub assembly defining a respective longitudinal axis. The distal hub assembly includes a proximal bracket pivotally connected to the proximal hub; and a distal bracket pivotally connected to the proximal bracket, the distal bracket being rotatable relative to the proximal bracket along the longitudinal axis of the distal hub assembly.

The end effector further includes a jaw assembly including a pair of jaws pivotally supported on the distal bracket. Each jaw includes a proximal portion pivotally connected to the distal bracket; and a distal portion extending distally of the proximal portion thereof.

The end effector also includes at least one gear train supported in the wrist assembly. The at last one gear train transmits forces from the at least one motor of the control device to at least one of the proximal bracket of the wrist assembly, the distal bracket of the wrist assembly and the jaw assembly. The gear train enables at least one of a pivoting of the distal hub assembly relative to the proximal hub; a rotation of the distal bracket relative to the proximal bracket; and an opening/closing of the jaw assembly.

The at least one gear train may include a first gear train comprising a first gear rotatably supported in the proximal hub, the first gear of the proximal hub being in operative communication with at least one motor of the control system; and a first gear non-rotatably supported on the proximal bracket of the distal hub assembly. The first gear of the proximal bracket may define a rotation axis that is co-axial with a pivot axis of the distal hub assembly relative to the proximal hub. The first gear of the proximal bracket may be in meshing engagement with the first gear of the proximal hub.

The at least one gear train may include a second gear train comprising a second gear rotatably supported in the proximal hub, the second gear of the proximal hub being in operative communication with at least one motor of the control system, the first gear and the second gear of the proximal hub being concentric; a second gear rotatably supported in the proximal bracket of the distal hub assembly, wherein the first gear and the second gear of the proximal bracket are concentric; and a further second gear rotatably supported in the proximal bracket of the distal hub assembly, wherein the further second gear defines a rotation axis that is co-axial with the longitudinal axis of the distal hub assembly, the further second gear being non-rotatably supported on a stem extending from the distal bracket.

The further second gear of the proximal bracket may be in meshing engagement with the second gear of the proximal bracket. The second gear of the proximal bracket may be in meshing engagement with the second gear of the proximal hub.

The at least one gear train may include a third gear train comprising a third gear rotatably supported in the proximal hub, the third gear of the proximal hub being in operative communication with at least one motor of the control system, the first, second and third gears of the proximal hub being concentric with one another; a third gear rotatably supported in the proximal bracket of the distal hub assembly, wherein the first, second and third gears of the proximal bracket are concentric with one another; and a further third gear rotatably supported in the proximal bracket of the distal hub assembly, wherein the further third gear is co-axial and concentric with the further second gear of the proximal bracket, the further third gear being non-rotatably supported on a stem extending from a gear rotatably supported in the distal bracket.

The further third gear of the proximal bracket may be in meshing engagement with the third gear of the proximal bracket. The third gear of the proximal bracket may be in meshing engagement with the third gear of the proximal hub.

The at least one gear train may include a gear rotatably supported in the distal bracket of the distal hub assembly. The gear of the distal bracket may be keyed to the further third gear of the proximal bracket. The proximal portion of each jaw may be in meshing engagement with the gear of the distal bracket.

The first gear that is rotatably supported in the proximal hub may define a first diameter. The second gear that is rotatably supported in the proximal hub may define a second diameter smaller than the first diameter. The third gear that is rotatably supported in the proximal hub may define a third diameter that is smaller than the second diameter.

The first gear that is non-rotatably supported on the proximal bracket may define a first diameter. The second gear that is rotatably supported on the proximal bracket may define a second diameter smaller than the first diameter. The third gear that is rotatably supported on the proximal bracket may define a third diameter that is smaller than the second diameter.

The further second gear that is rotatably supported on the proximal bracket may define a diameter. The further third gear that is rotatably supported in the proximal bracket may define a diameter that is smaller than the diameter of the further second gear.

The proximal bracket may be U-shaped including a pair of spaced apart upright supports extending in a proximal direction that are interconnected by a backspan. The first gear that is non-rotatably supported on the proximal bracket and the second and third gears that are rotatably supported on the proximal bracket may be supported on one of the proximally extending upright supports of the proximal bracket.

The further second gear and the further third gear, that are rotatably supported on the proximal bracket, may be supported on the backspan of the proximal bracket.

The end effector may further comprise a first drive tube extending through the proximal hub and supporting the first gear on a distal end thereof, the first drive tube defining a lumen therethrough; a second drive tube extending through the proximal hub and through the lumen of the first drive tube, the second drive tube supporting the second gear on a distal end thereof, the second drive tube defining a lumen therethrough; and a third drive tube extending through the proximal hub and through the lumen of the second drive tube, the third drive tube supporting the third gear on a distal end thereof.

The first gear that is rotatably supported in the proximal hub may define a first diameter. The second gear that is rotatably supported in the proximal hub may define a second diameter smaller than the first diameter. The third gear that is rotatably supported in the proximal hub may define a third diameter that is smaller than the second diameter.

According to another aspect of the present disclosure, an end effector for use and connection to a robot arm of a robotic surgical system is provided, wherein the end effector is controlled and/or articulated by at least one motor of a control device of the robot surgical system. The end effector comprises a wrist assembly including a proximal hub defining a respective longitudinal axis; and a distal hub assembly.

The distal assembly includes a proximal bracket pivotally connected to the proximal hub, wherein the proximal bracket defines a longitudinal axis, and wherein the proximal bracket is pivotable about a first pivot axis that extends transversely to the longitudinal axis of the proximal hub. The distal assembly further includes a distal bracket pivotally connected to the proximal bracket, wherein the distal bracket defines a longitudinal axis, and wherein the distal bracket is pivotable about a second pivot axis that extends transversely to the longitudinal axis of the proximal hub and transversely to the first pivot axis.

The end effector comprises a jaw assembly including a pair of jaws pivotally supported on the distal bracket. Each jaw includes a proximal portion pivotally connected to the distal bracket; and a distal portion extending distally of the proximal portion thereof.

The end effector further includes at least one gear train supported in the wrist assembly, wherein the at last one gear train transmits forces from the at least one motor of the control device to at least one of the proximal bracket of the wrist assembly, the distal bracket of the wrist assembly and the jaw assembly. The gear train enabling at least one of a pivoting of the proximal bracket relative to the proximal hub; a pivoting of the distal bracket relative to the proximal bracket; and an opening/closing of the jaw assembly.

The at least one gear train may include a first gear train comprising a first gear rotatably supported in the proximal hub, the first gear of the proximal hub being in operative communication with at least one motor of the control system; and a first gear non-rotatably supported on the proximal bracket of the distal hub assembly. The first gear of the proximal bracket may define a rotation axis that is co-axial with the first pivot axis. The first gear of the proximal bracket may be in meshing engagement with the first gear of the proximal hub.

The at least one gear train may include a second gear train comprising a second gear rotatably supported in the proximal hub, wherein the second gear of the proximal hub is in operative communication with at least one motor of the control system, and wherein the first gear and the second gear of the proximal hub may be concentric. The second gear train may include a second gear rotatably supported in the proximal bracket and along the first pivot axis, wherein the first gear and the second gear of the proximal bracket may be concentric.

The second gear train may further include a proximal second gear rotatably supported in the proximal bracket of the distal hub assembly and along the longitudinal axis of the proximal bracket; a distal second gear rotatably supported in the proximal bracket of the distal hub assembly and along the longitudinal axis of the proximal bracket, wherein the proximal second gear and the distal second gear may be non-rotatably supported on a common shaft; and a second gear non-rotatably supported on the distal bracket of the distal hub assembly, wherein the second gear of the distal bracket defines a rotation axis that is co-axial with the second pivot axis, wherein the second gear of the distal bracket may be in meshing engagement with the distal second gear of the proximal hub.

The at least one gear train may include a third gear train comprising a third gear rotatably supported in the proximal hub. The third gear of the proximal hub may be in operative communication with at least one motor of the control system. The first, second and third gears of the proximal hub may be concentric with one another.

The third gear train may also include a proximal third gear rotatably supported in the proximal bracket of the distal hub assembly and along the longitudinal axis of the proximal bracket; a distal third gear rotatably supported in the proximal bracket of the distal hub assembly and along the longitudinal axis of the proximal bracket, wherein the proximal third gear and the distal third gear of the proximal bracket may be non-rotatably supported on a common shaft; a third gear rotatably supported on the distal bracket of the distal hub assembly, wherein the third gear of the distal bracket defines a rotation axis that is co-axial with the second pivot axis, wherein the third gear of the distal bracket may be in meshing engagement with the distal third gear of the proximal bracket; a proximal third gear rotatably supported in the distal bracket of the distal hub assembly and along the longitudinal axis of the distal bracket, the proximal third gear that is supported in the distal bracket may be in meshing engagement with the third gear rotatably supported on the second pivot axis of the distal bracket; and a distal third gear rotatably supported in the distal bracket of the distal hub assembly and along the longitudinal axis of the distal bracket, wherein the proximal third gear and the distal third gear of the distal bracket may be non-rotatably supported on a common shaft.

The proximal portion of each jaw may be in meshing engagement with the distal third gear rotatably supported in the distal bracket.

The first gear that is rotatably supported in the proximal hub may define a first diameter. The second gear that is rotatably supported in the proximal hub may define a second diameter smaller than the first diameter. The third gear that is rotatably supported in the proximal hub may define a third diameter that is smaller than the second diameter.

The first gear that is non-rotatably supported on the proximal bracket may define a first diameter. The second gear that is rotatably supported on the first pivot axis of the proximal bracket may define a second diameter smaller than the first diameter. The third gear that is rotatably supported on the first pivot axis of the proximal bracket may define a third diameter that is smaller than the second diameter.

The proximal second gear that is rotatably supported in the proximal bracket may define a diameter. The proximal third gear that is rotatably supported in the proximal bracket may define a diameter that is smaller than the diameter of the proximal second gear that is rotatably supported in the proximal bracket of the distal hub assembly.

The second gear that is non-rotatably supported on the distal bracket may define a diameter. The third gear that is rotatably supported on the distal bracket may define a diameter that is smaller that the diameter of the second gear that is non-rotatably supported on the distal bracket.

Further details and aspects of exemplary embodiments of the present disclosure are described in more detail below with reference to the appended figures.

BRIEF DESCRIPTION OF THE DRAWINGS

Embodiments of the present disclosure are described herein with reference to the accompanying drawings, wherein:

FIG. 5 is a perspective view of an end effector, according to another embodiment of the present disclosure, for use in the medical work station of FIG. 1A, illustrating a jaw assembly thereof in a non-articulated and a closed condition;

FIG. 6 is a perspective view of the end effector of FIG. 5 illustrating the jaw assembly thereof in an articulated and an open condition;

FIG. 8 is a perspective view of an end effector, according to another embodiment of the present disclosure, for use in the medical work station of FIG. 1A, illustrating a jaw assembly thereof in a non-articulated and a closed condition;

FIG. 9 is a perspective view of the end effector of FIG. 8 illustrating the jaw assembly thereof in an articulated and an open condition.

DETAILED DESCRIPTION

Figure 1A:
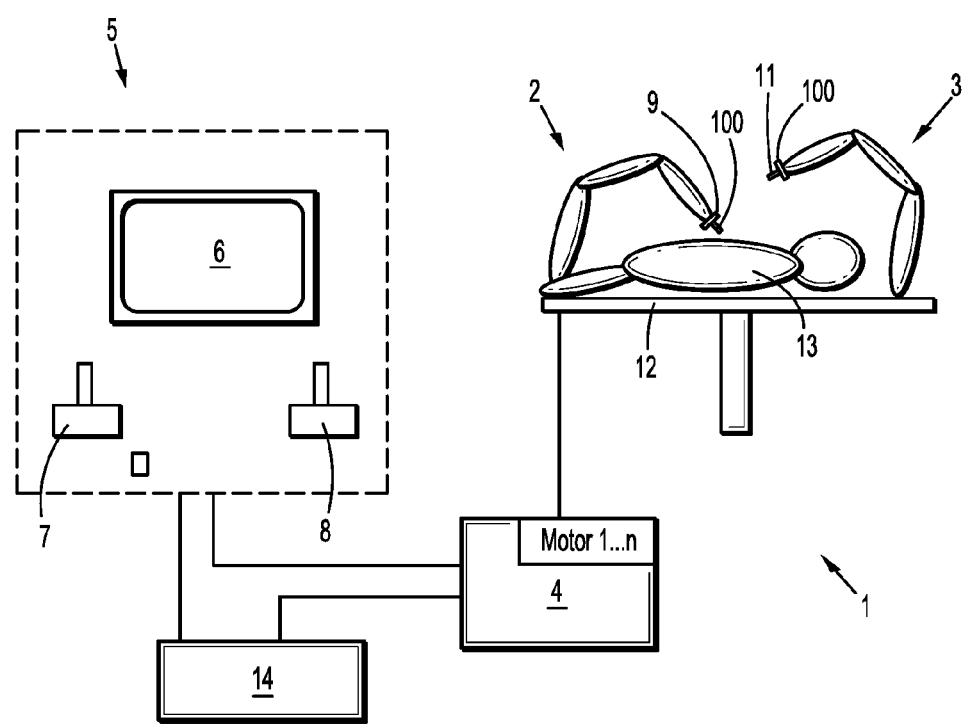
FIG. 1A is a schematic illustration of a medical work station and operating console in accordance with the present disclosure.

Embodiments of the presently disclosed jaw assemblies and/or wrist assemblies are described in detail with reference to the drawings, in which like reference numerals designate identical or corresponding elements in each of the several views. As used herein the term "distal" refers to that portion of the jaw assembly and/or wrist assembly, that is farther from the user, while the term "proximal" refers to that portion of the jaw assembly and/or wrist assembly that is closer to the user.

Figure 1B:
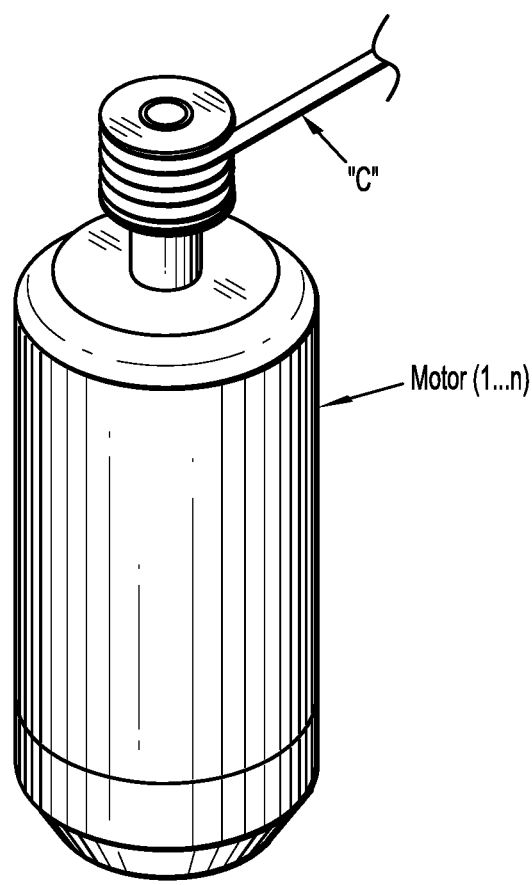
FIG. 1B is a schematic, perspective view of a motor of a control device of the medical work station of FIG. 1A.

Referring initially to FIGS. 1A and 1B, a medical work station is shown generally as work station 1 and generally includes a plurality of robot arms 2, 3; a control device 4; and an operating console 5 coupled with control device 4. Operating console 5 includes a display device 6, which is set up in particular to display three-dimensional images; and manual input devices 7, 8, by means of which a person (not shown), for example a surgeon, is able to telemanipulate robot arms 2, 3 in a first operating mode, as known in principle to a person skilled in the art.

Each of the robot arms 2, 3 includes a plurality of members, which are connected through joints, and an attaching device 9, 11, to which may be attached, for example, a surgical tool "ST" supporting an end effector 100, in accordance with any one of several embodiments disclosed herein, as will be described in greater detail below.

Robot arms 2, 3 may be driven by electric drives (not shown) that are connected to control device 4. Control device 4 (e.g., a computer) is set up to activate the drives, in particular by means of a computer program, in such a way that robot arms 2, 3, their attaching devices 9, 11 and thus the surgical tool (including end effector 100) execute a desired movement according to a movement defined by means of manual input devices 7, 8. Control device 4 may also be set up in such a way that it regulates the movement of robot arms 2, 3 and/or of the drives.

Medical work station 1 is configured for use on a patient 13 lying on a patient table 12 to be treated in a minimally invasive manner by means of end effector 100. Medical work station 1 may also include more than two robot arms 2, 3, the additional robot arms likewise being connected to control device 4 and being telemanipulatable by means of operating console 5. A medical instrument or surgical tool (including an end effector 100) may also be attached to the additional robot arm.

Reference may be made to U.S. Patent Publication No. 2012/0116416, filed on Nov. 3, 2011, entitled "Medical Workstation," the entire content of which is incorporated herein by reference, for a detailed discussion of the construction and operation of medical work station 1.

Control device 4 may control a plurality of motors (Motor 1 . . . n) with each motor configured to wind-up or let out a length of a cable "C" (FIG. 1B) extending through each robot arm to end effector 100 of the surgical tool, or to rotate a gear or a drive shaft (not shown). In use, as cables "C" are wound-up and let out, cables "C", gears or drive shafts may effect operation and/or movement of each end effector of the surgical tool. It is contemplated that control device 4 coordinates the activation of the various motors (Motor 1 . . . n) to coordinate a winding-up or letting out a length of a respective cable "C" in order to coordinate an operation and/or movement of a respective end effector. Although FIG. 1B shows a single cable "C" that is wound up or let out by a single motor, in some instances two or more cables or two ends of a single cable may be wound up or let out by a single motor. For example, in some instances, two cables or cable ends may be coupled in opposite directions to a single motor so that as the motor is activated in a first direction, one of the cables winds up while the other cable lets out. Other cable configurations may be used in different embodiments.

Figures 2, 3:
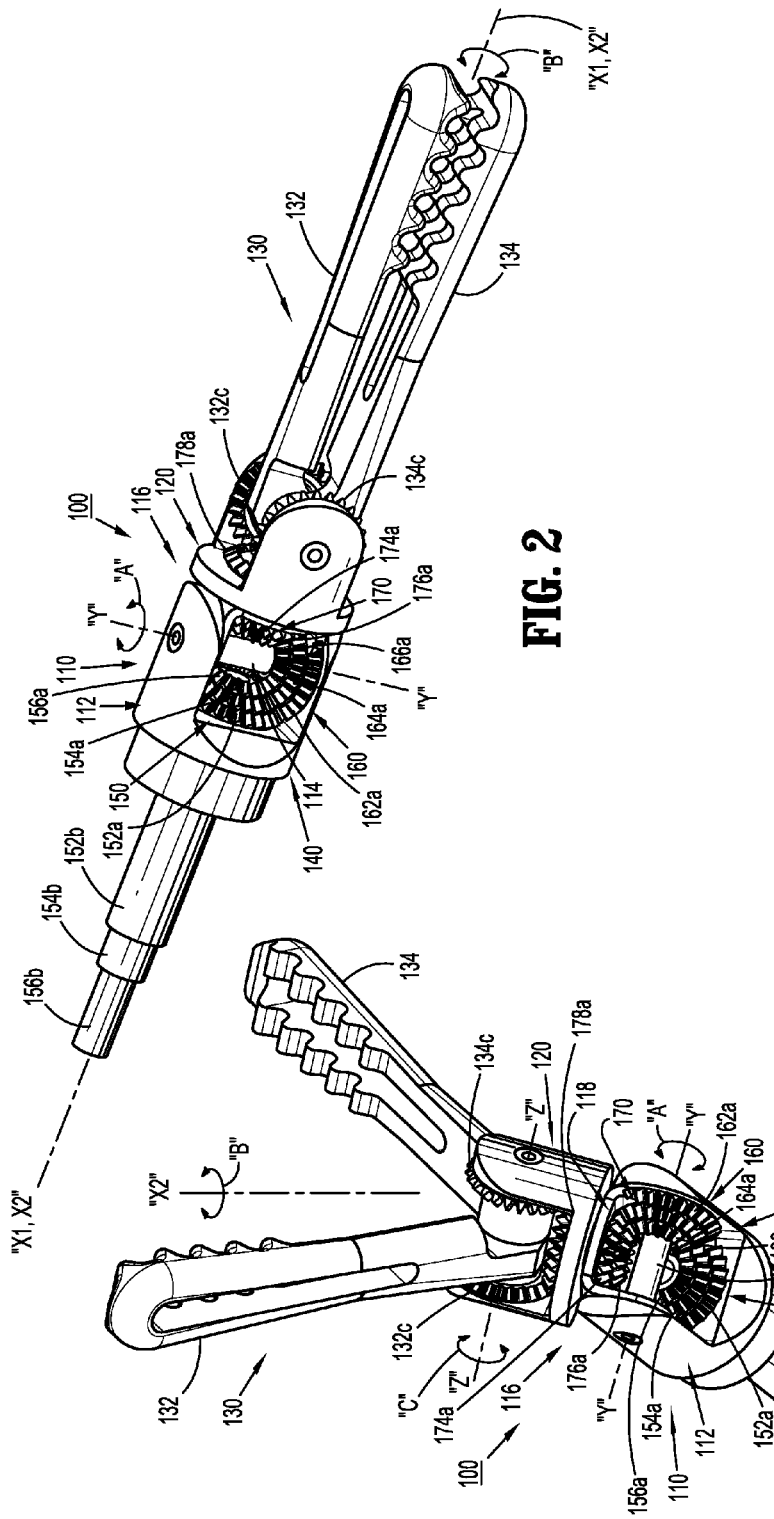
FIG. 2 is a perspective view of an end effector, according to an embodiment of the present disclosure, for use in the medical work station of FIG. 1A, illustrating a jaw assembly thereof in a non-articulated and a closed condition.
FIG. 3 is a perspective view of the end effector of FIG. 2 illustrating the jaw assembly thereof in an articulated and an open condition.
Figure 4:
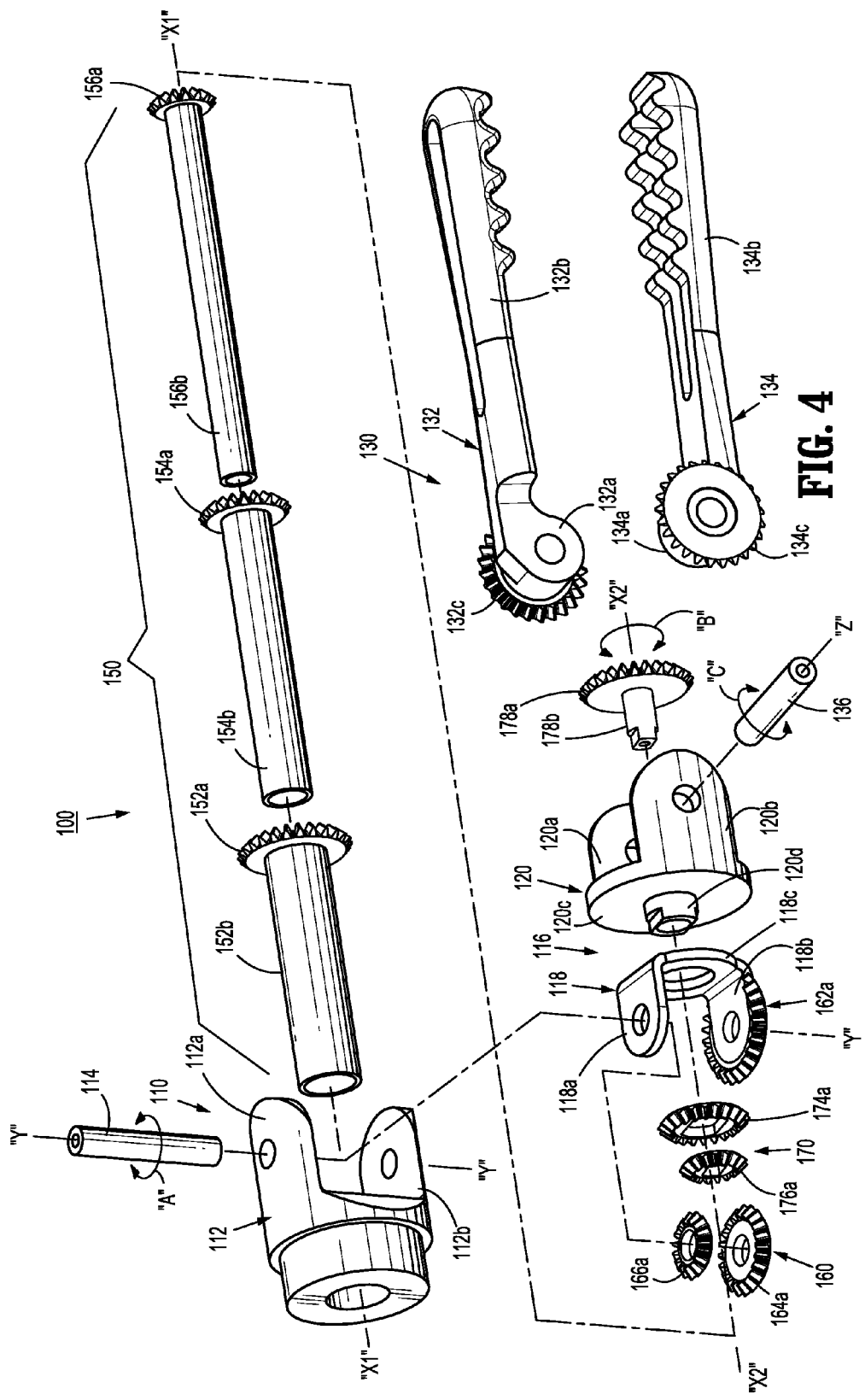
FIG. 4 is a perspective view, with parts separated, of the end effector of FIGS. 2 and 3.

Turning now to FIGS. 2-4, an end effector for connection to robot arms 2, 3 and for manipulation by control device 4, is generally designated as 100. End effector 100 includes a wrist assembly 110, and a jaw assembly 130 pivotally connected to wrist assembly 110. Wrist assembly 110 includes a proximal hub 112, in the form of a distally extending clevis, defining a first longitudinal axis "X1-X1." Proximal hub 112 defines a first pivot axis "Y-Y" that is oriented orthogonal to the first longitudinal axis "X1-X1." In an embodiment, first pivot axis "Y-Y" may extend through the first longitudinal axis "X1-X1." Proximal hub 112, being in the form of a clevis, includes a pair of spaced apart, opposed upright supports 112a, 112b through which first pivot axis "Y-Y" extends.

Wrist assembly 110 further includes a distal hub assembly 116 pivotally connected to upright supports 112a, 112b of proximal hub 112. Distal hub assembly 116 includes a proximal U-shaped bracket 118 having a pair of spaced apart, opposed, proximally extending, upright supports 118a, 118b interconnected by a backspan 118c. Upright supports 118a, 118b of proximal U-shaped bracket 118 are pivotally connected to respective upright supports 112a, 112b of proximal hub 112, via a pivot pin 114. Pivot pin 114 is disposed along first pivot axis "Y-Y".

Distal hub assembly 116 further includes a distal U-shaped bracket 120 having a pair of spaced apart, opposed, distally extending, upright supports 120a, 120b interconnected by a backspan 120c. Upright supports 120a, 120b of distal U-shaped bracket 120 define a second pivot axis "Z-Z" therebetween. Backspan 120c of distal U-shaped bracket 120 is pivotally connected to backspan 118c of proximal U-shaped bracket 118, about a second longitudinal axis "X2-X2." Second pivot axis "Z-Z" is oriented orthogonal to the first longitudinal axis "X1-X1." In an embodiment, when the first longitudinal axis "X1-X1" is parallel with the second longitudinal axis "X2-X2" (i.e., end effector 100 is in an axially aligned orientation), second pivot axis "Z-Z" may extend through first longitudinal axis "X1-X1."

With continued reference to FIGS. 2-4, as mentioned above, end effector 100 includes a jaw assembly 130 that is pivotally supported on a pivot pin 136 extending between upright supports 120a, 120b of distal U-shaped bracket 120 and along second pivot axis "B-B". Jaw assembly 130 includes a pair of jaws 132, 134 pivotally connected to upright supports 120a, 120b of distal U-shaped bracket 120. Specifically, each jaw 132, 134 includes a respective proximal end 132a, 134a pivotally connected to upright supports 120a, 120b of distal U-shaped bracket 120, via pivot pin 136; and a respective distal end 132b, 134b. Each distal end 132b, 134b of the pair of jaws 132, 134 defines a grip or toothed portion in juxtaposed relation to one another.

In accordance with the present disclosure and the present embodiment, end effector 100 includes a gear system 140 configured and adapted to transfer/transmit rotational forces generated by motors (Motor 1 . . . n) of control device 4 into an articulation of wrist assembly 110 along first pivot axis "Y-Y", a rotation of jaw assembly 130 along second longitudinal axis "X2-X2", and an opening/closing of jaw assembly 130.

Gear system 140 includes a first gear assembly 150 rotatably supported in proximal hub 112 of wrist assembly 110. First gear assembly 150 includes a first or outer bevel gear 152a supported on a distal end of a first or outer drive tube 152b. Outer bevel gear 152a defines a first or relatively large diameter. Outer drive tube 152b defines a lumen therethrough having a longitudinal axis that is coaxial or parallel with the first longitudinal axis "X1-X1". A proximal end of outer drive tube 152a may be acted upon, either directly or indirectly, by a respective motor (Motor 1 . . . n) of control device 4 so as to be rotated about the longitudinal axis thereof.

First gear assembly 150 also includes a second or intermediate bevel gear 154a supported on a distal end of a second or intermediate drive tube 154b. Intermediate bevel gear 154a defines a second or relatively intermediate diameter that is smaller than the diameter of outer bevel gear 152a. Intermediate drive tube 154b defines a lumen therethrough having a longitudinal axis that is coaxial or parallel with the first longitudinal axis "X1-X1". Intermediate drive tube 154b is sized and dimensioned to be rotatably disposed within the lumen of outer drive tube 152b. A proximal end of intermediate drive tube 154a may be acted upon, either directly or indirectly, by a respective motor (Motor 1 . . . n) of control device 4 so as to be rotated about the longitudinal axis thereof.

First gear assembly 150 further also includes a third or inner bevel gear 156a supported on a distal end of a third or inner drive tube 156b. Inner bevel gear 156a defines a third or relatively small diameter that is smaller than the diameter of intermediate bevel gear 154a. Inner drive tube 156b defines a lumen therethrough having a longitudinal axis that is coaxial or parallel with the first longitudinal axis "X1-X1". Inner drive tube 156b is sized and dimensioned to be rotatably disposed within the lumen of intermediate drive tube 154b. A proximal end of inner drive tube 156a may be acted upon, either directly or indirectly, by a respective motor (Motor 1 . . . n) of control device 4 so as to be rotated about the longitudinal axis thereof.

As illustrated in FIGS. 2-4, bevel gears 152a, 154a, and 156a of first gear assembly 150 are arranged in a stacked and concentric configuration, wherein intermediate bevel gear 154a is stacked or disposed distal of and concentric with outer bevel gear 152a, and inner bevel gear 156a is stacked or disposed distal of and concentric with intermediate bevel gear 154a.

Gear system 140 includes a second gear assembly 160 rotatably supported in/on proximal U-shaped bracket 118 of distal hub assembly 116, and rotatably supported on pivot pin 114. Specifically, second gear assembly 160 includes a first or outer bevel gear 162a non-rotatably supported on or integrally formed in one of upright supports 118a, 118b of proximal U-shaped bracket 118. Outer bevel gear 162a of second gear assembly 160 defines a first or relatively large diameter. Outer bevel gear 162a of second gear assembly 160 is in meshing engagement with outer bevel gear 152a of first gear assembly 150.

Second gear assembly 160 also includes a second or intermediate bevel gear 164a rotatably supported on pivot pin 114. Intermediate bevel gear 164a of second gear assembly 160 defines a second or intermediate diameter. Intermediate bevel gear 164a of second gear assembly 160 is in meshing engagement with intermediate bevel gear 154a of first gear assembly 150.

Second gear assembly 160 further includes a third or inner bevel gear 166a rotatably supported on pivot pin 114. Inner bevel gear 166a of second gear assembly 160 defines a third or small diameter. Inner bevel gear 166a of second gear assembly 160 is in meshing engagement with inner bevel gear 156a of first gear assembly 150.

Bevel gears 162a, 164a, and 166a of second gear assembly 160 are arranged in a stacked and concentric configuration, wherein intermediate bevel gear 164a is stacked or disposed atop and concentric with outer bevel gear 162a, and inner bevel gear 166a is stacked atop and concentric with intermediate bevel gear 164a.

Gear system 140 includes a third gear assembly 170 rotatably supported in/on proximal U-shaped bracket 118 of distal hub assembly 116, specifically on backspan 118c of proximal U-shaped bracket 118, between upright supports 118a, 118b. Third gear assembly 170 includes an intermediate bevel gear 174a keyed to or non-rotatably supported on a stem 120d extending from backspan 120c of distal U-shaped bracket 120 that extends through backspan 118c of proximal U-shaped bracket 118. Intermediate bevel gear 174a is axially disposed along second longitudinal axis "X2-X2". Intermediate bevel gear 174a of third gear assembly 170 defines an intermediate diameter. Intermediate bevel gear 174a of third gear assembly 170 is in meshing engagement with intermediate bevel gear 164a of second gear assembly 160.

Third gear assembly 170 further includes an inner bevel gear 176a keyed to or non-rotatably supported on a stem 178b extending from a jaw bevel gear 178a rotatably disposed between upright supports 120a, 120b of distal U-shaped bracket 120. Stem 178b extends through backspan 120c of distal U-shaped bracket 120, through backspan 118c of proximal U-shaped bracket 118, and through intermediate bevel gear 174a of third gear assembly 170. Inner bevel gear 176a is axially disposed along second longitudinal axis "X2-X2". Inner bevel gear 176a of third gear assembly 170 defines a small diameter. Inner bevel gear 176a of third gear assembly 170 is in meshing engagement with inner bevel gear 166a of second gear assembly 160.

Bevel gears 174a and 176a of third gear assembly 170 are arranged in a stacked and concentric configuration, wherein inner bevel gear 176a is stacked or disposed proximal of and concentric with intermediate bevel gear 174a.

As illustrated in FIGS. 2-4, proximal end 132a of jaw 132 defines or non-rotatably supports a bevel gear 132c, and proximal end 134a of jaw 134 defines or non-rotatably supports a bevel gear 134c. Each bevel gear 132c, 134c is in meshing engagement with jaw bevel gear 178a.

In accordance with the present disclosure, a first gear train is defined which includes outer bevel gear 152a of first gear assembly 150, and outer bevel gear 162a of second gear assembly 160. Also, a second gear train is defined which includes intermediate bevel gear 154a of first gear assembly 150, intermediate bevel gear 164a of second gear assembly 160, and intermediate bevel gear 174a of third gear assembly 170. Further, a third gear train is defined which includes inner bevel gear 156a of first gear assembly 150, inner bevel gear 166a of second gear assembly 160, inner bevel gear 176a of third gear assembly 170, jaw bevel gear 178, and bevel gears 132c, 134c of jaws 132, 134.

In operation, when the first gear train is actuated, end effector 100 is pivoted or articulated about first pivot axis "Y-Y". Specifically, in operation, rotation of outer tube 152b results in rotation of outer bevel gear 152a of first gear assembly 150, which results in rotation of outer bevel gear 162a of second gear assembly 160 to rotate proximal U-shaped bracket 118 of distal hub assembly 116 about first pivot axis "Y-Y" and thus pivot jaws 132, 134 about first pivot axis "Y-Y", as indicated by arrow "A".

Also in operation, when the second gear train is actuated, end effector 100 is rotated along second longitudinal axis "X2-X2". Specifically, in operation, rotation of intermediate tube 154b results in rotation of intermediate bevel gear 154a of first gear assembly 150, which results in rotation of intermediate bevel gear 164a of second gear assembly 160, which results in rotation of intermediate bevel gear 174a of third gear assembly 170 to rotate distal U-shaped bracket 120 of distal hub assembly 116 about second longitudinal axis "X2-X2" and thus rotate jaws 132, 134 about second longitudinal axis "X2-X2", as indicated by arrow "B".

Additionally, in operation, when the third gear train is actuated, end effector 100 actuated to open/close jaws 132, 134. Specifically, in operation, rotation of inner tube 156b results in rotation of inner bevel gear 156a of first gear assembly 150, which results in rotation of inner bevel gear 166a of second gear assembly 160, which results in rotation of inner bevel gear 176a of third gear assembly 170, which results in rotation of jaw bevel gear 178a, and which results in opposed rotations of bevel gears 132c, 134c of jaws 132, 134 about second pivot axis "Z", as indicated by arrow "C", resulting in an opening or closing of jaws 132, 134.

Figure 7:
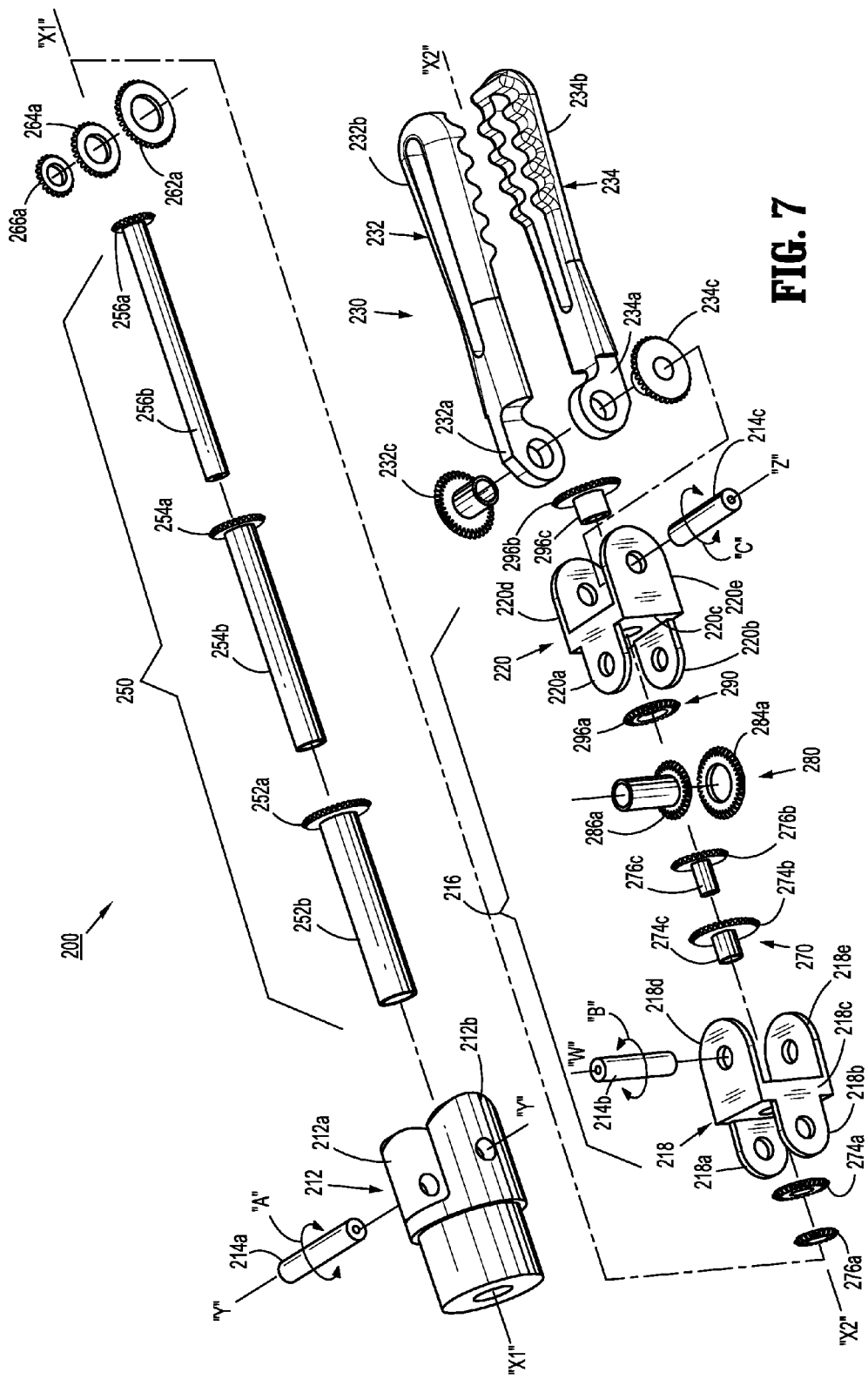
FIG. 7 is a perspective view, with parts separated, of the end effector of FIGS. 5 and 6.

Turning now to FIGS. 5-7, an end effector for connection to robot arms 2, 3 and for manipulation by control device 4, in accordance with another embodiment of the present disclosure, is generally designated as 200.

End effector 200 includes a wrist assembly 210, and a jaw assembly 230 pivotally connected to wrist assembly 210. Wrist assembly 210 includes a proximal hub 212, in the form of a distally extending clevis, defining a first longitudinal axis "X1-X1." Proximal hub 212 defines a first pivot axis "Y-Y" that is oriented orthogonal to the first longitudinal axis "X1-X1." In an embodiment, first pivot axis "Y-Y" may extend through the first longitudinal axis "X1-X1." Proximal hub 212, being in the form of a clevis, includes a pair of spaced apart, opposed upright supports 212a, 212b through which first pivot axis "Y-Y" extends.

Wrist assembly 210 further includes a distal hub assembly 216 pivotally connected to upright supports 212a, 212b of proximal hub 212. Distal hub assembly 216 includes a proximal bracket 218 having a pair of spaced apart, opposed, proximally extending, upright supports 218a, 218b interconnected by a backspan 218c, and a pair of spaced apart, opposed, distally extending, upright supports 218d, 218e interconnected by backspan 218c. Proximal upright supports 218a, 218b of proximal bracket 218 are pivotally connected to respective upright supports 212a, 212b of proximal hub 212, via a first pivot pin 214a. First pivot pin 214a defines a first pivot axis "Y-Y".

Distal hub assembly 216 further includes a distal bracket 220 having a pair of spaced apart, opposed, proximally extending, upright supports 220a, 220b interconnected by a backspan 220c, and a pair of spaced apart, opposed, distally extending, upright supports 220d, 220e interconnected by backspan 220c. Proximal upright supports 220a, 220b of distal bracket 220 are pivotally connected to respective upright supports 218d, 218e of proximal bracket 218, via a second pivot pin 214b. Second pivot pin 214b defines a second pivot axis "W-W". Distal bracket 220 defines a second longitudinal axis "X2-X2." Second pivot axis "W-B" is oriented orthogonal to the first longitudinal axis "X1-X1."

With continued reference to FIGS. 5-7, as mentioned above, end effector 200 includes a jaw assembly 230 that is pivotally supported on a third pivot pin 214c extending between upright supports 220d, 220e of distal bracket 220 and along a third pivot axis "Z-Z". Jaw assembly 230 includes a pair of jaws 232, 234 pivotally connected to upright supports 220d, 220e of distal bracket 220. Specifically, each jaw 232, 234 includes a respective proximal end 232a, 234a pivotally connected to upright supports 220d, 220e of distal bracket 220, via third pivot pin 214c; and a respective distal end 232b, 234b. Each distal end 232b, 234b of the pair of jaws 232, 234 defines a grip or toothed portion in juxtaposed relation to one another.

In accordance with the present disclosure and the present embodiment, end effector 200 includes a gear system 240 (FIG. 6) configured and adapted to transfer/transmit rotational forces generated by motors (Motor 1 . . . n) of control device 4 into an articulation of wrist assembly 210 along first pivot axis "Y-Y", an articulation of wrist assembly 210 along second pivot axis "W-W", and an opening/closing of jaw assembly 230.

Gear system 240 includes a first gear assembly 250 rotatably supported in proximal hub 212 of wrist assembly 210. First gear assembly 250 includes a first or outer bevel gear 252a supported on a distal end of a first or outer drive tube 252b. Outer bevel gear 252a defines a first or relatively large diameter. Outer drive tube 252b defines a lumen therethrough having a longitudinal axis that is coaxial or parallel with the first longitudinal axis "X1-X1". A proximal end of outer drive tube 252a may be acted upon, either directly or indirectly, by a respective motor (Motor 1 . . . n) of control device 4 so as to be rotated about the longitudinal axis thereof.

First gear assembly 250 also includes a second or intermediate bevel gear 254a supported on a distal end of a second or intermediate drive tube 254b. Intermediate bevel gear 254a defines a second or relatively intermediate diameter that is smaller than the diameter of outer bevel gear 252a. Intermediate drive tube 254b defines a lumen therethrough having a longitudinal axis that is coaxial or parallel with the first longitudinal axis "X1-X1". Intermediate drive tube 254b is sized and dimensioned to be rotatably disposed within the lumen of outer drive tube 252b. A proximal end of intermediate drive tube 254a may be acted upon, either directly or indirectly, by a respective motor (Motor 1 . . . n) of control device 4 so as to be rotated about the longitudinal axis thereof.

First gear assembly 250 further also includes a third or inner bevel gear 256a supported on a distal end of a third or inner drive tube 256b. Inner bevel gear 256a defines a third or relatively small diameter that is smaller than the diameter of intermediate bevel gear 254a. Inner drive tube 256b defines a lumen therethrough having a longitudinal axis that is coaxial or parallel with the first longitudinal axis "X1-X1". Inner drive tube 256b is sized and dimensioned to be rotatably disposed within the lumen of intermediate drive tube 254b. A proximal end of inner drive tube 256a may be acted upon, either directly or indirectly, by a respective motor (Motor 1 . . . n) of control device 4 so as to be rotated about the longitudinal axis thereof.

As illustrated in FIGS. 5-7, bevel gears 252a, 254a, and 256a of first gear assembly 250 are arranged in a stacked and concentric configuration, wherein intermediate bevel gear 254a is stacked or disposed distal of and concentric with outer bevel gear 252a, and inner bevel gear 256a is stacked or disposed distal of and concentric with intermediate bevel gear 254a.

Gear system 240 includes a second gear assembly 260 rotatably supported in/on proximal bracket 218 of distal hub assembly 216, and rotatably supported on first pivot pin 214a. Specifically, second gear assembly 260 includes a first or outer bevel gear 262a non-rotatably supported on or integrally formed in one of proximal upright supports 218a, 218b of proximal bracket 218. Outer bevel gear 262a of second gear assembly 260 defines a first or relatively large diameter. Outer bevel gear 262a of second gear assembly 260 is in meshing engagement with outer bevel gear 252a of first gear assembly 250.

Second gear assembly 260 also includes a second or intermediate bevel gear 264a rotatably supported on first pivot pin 214a. Intermediate bevel gear 264a of second gear assembly 260 defines a second or intermediate diameter. Intermediate bevel gear 264a of second gear assembly 260 is in meshing engagement with intermediate bevel gear 254a of first gear assembly 250.

Second gear assembly 260 further includes a third or inner bevel gear 266a rotatably supported on first pivot pin 214a. Inner bevel gear 266a of second gear assembly 260 defines a third or small diameter. Inner bevel gear 266a of second gear assembly 260 is in meshing engagement with inner bevel gear 256a of first gear assembly 250.

Bevel gears 262a, 264a, and 266a of second gear assembly 260 are arranged in a stacked and concentric configuration, wherein intermediate bevel gear 264a is stacked or disposed atop and concentric with outer bevel gear 262a, and inner bevel gear 266a is stacked atop and concentric with intermediate bevel gear 264a.

Gear system 240 includes a third gear assembly 270 rotatably supported in/on proximal bracket 218 of distal hub assembly 216, specifically on backspan 218c of proximal bracket 218, between upright supports 218a, 218b and between upright supports 218d, 218e. Third gear assembly 270 includes a proximal intermediate bevel gear 274a keyed to or non-rotatably supported on a stem 274c, that extends through backspan 218c, and which non-rotatably supports a distal intermediate bevel gear 274b.

Proximal and distal intermediate bevel gears 274a, 274b are axially disposed along second longitudinal axis "X2-X2". Proximal and distal intermediate bevel gears 274a, 274b of third gear assembly 270 each define an intermediate diameter. Proximal intermediate bevel gear 274a of third gear assembly 270 is in meshing engagement with intermediate bevel gear 264a of second gear assembly 260.

Third gear assembly 270 further includes a proximal inner bevel gear 276a keyed to or non-rotatably supported on a stem 276c, that extends through stem 274c and through backspan 218c, and which non-rotatably supports a distal inner bevel gear 276b. Proximal and distal inner bevel gears 276a, 276b are axially disposed along second longitudinal axis "X2-X2". Proximal and distal inner bevel gears 276a, 276b of third gear assembly 270 each define a small diameter. Proximal inner bevel gear 276a of third gear assembly 270 is in meshing engagement with inner bevel gear 266a of second gear assembly 260.

Proximal bevel gears 274a and 276a of third gear assembly 270 are arranged in a stacked and concentric configuration, wherein proximal inner bevel gear 276a is stacked or disposed proximal of and concentric with proximal intermediate bevel gear 274a, and wherein distal inner bevel gear 276b is stacked or disposed distal of and concentric with distal intermediate bevel gear 274b.

Gear system 240 additionally includes a fourth gear assembly 280 rotatably supported in/on proximal bracket 218 of distal hub assembly 216, and rotatably supported on second pivot pin 214b. Specifically, fourth gear assembly 280 includes an intermediate bevel gear 284a rotatably supported on second pivot pin 214b, between distal upright supports 218d, 218e of proximal bracket 218. Specifically, intermediate bevel gear 284a of fourth gear assembly 280 is non-rotatably connected to one of distal upright supports 218d, 218e of proximal bracket 218 or is integrally formed therewith. Intermediate bevel gear 284a of fourth gear assembly 280 defines an intermediate diameter. Intermediate bevel gear 284a of fourth gear assembly 280 is in meshing engagement with distal intermediate bevel gear 274b of third gear assembly 270.

Fourth gear assembly 280 further includes an inner bevel gear 286a rotatably supported on second pivot pin 214b. Inner bevel gear 286a of fourth gear assembly 280 defines a small diameter. Inner bevel gear 286a of fourth gear assembly 280 is in meshing engagement with inner bevel gear 276b of third gear assembly 270.

Bevel gears 284a and 286a of fourth gear assembly 280 are arranged in a stacked and concentric configuration, wherein inner bevel gear 286a is stacked atop and concentric with intermediate bevel gear 284a.

Gear system 240 includes a fifth gear assembly 290 rotatably supported in/on distal bracket 220 of distal hub assembly 216, specifically on backspan 220c of distal bracket 220, between upright supports 220a, 220b and between upright supports 220d, 220e. Fifth gear assembly 290 includes a proximal inner bevel gear 296a keyed to or non-rotatably supported on a stem 296c, that extends through backspan 220c, and which non-rotatably supports a distal inner bevel gear 296b that is disposed distal of backspan 220c of distal bracket 220. Proximal and distal inner bevel gears 296a, 296b are axially disposed along second longitudinal axis "X2-X2". Proximal and distal inner bevel gears 296a, 296b of fifth gear assembly 290 each define a small diameter. Proximal inner bevel gear 296a of fifth gear assembly 290 is in meshing engagement with inner bevel gear 286a of fourth gear assembly 280.

As illustrated in FIGS. 5-7, proximal end 232a of jaw 232 defines or non-rotatably supports a bevel gear 232c, and proximal end 234a of jaw 234 defines or non-rotatably supports a bevel gear 234c. Each bevel gear 232c, 234c is in meshing engagement with distal inner bevel gear 296b of fifth gear assembly 290.

In accordance with the present disclosure, a first gear train is defined which includes outer bevel gear 252a of first gear assembly 250, and outer bevel gear 262a of second gear assembly 260. Also, a second gear train is defined which includes intermediate bevel gear 254a of first gear assembly 250, intermediate bevel gear 264a of second gear assembly 260, intermediate proximal bevel gear 274a and intermediate distal bevel gear 274b of third gear assembly 270, and intermediate bevel gear 284a of fourth gear assembly 280. Further, a third gear train is defined which includes inner bevel gear 256a of first gear assembly 250, inner bevel gear 266a of second gear assembly 260, inner proximal bevel gear 276a and inner distal bevel gear 276b of third gear assembly 270, inner bevel gear 286a of fourth gear assembly 280, inner proximal bevel gear 296a and inner distal bevel gear 296b of fifth gear assembly 290, and bevel gears 232c, 234c of jaws 232, 234.

In operation, when the first gear train is actuated, end effector 200 is pivoted or articulated about first pivot axis "Y-Y". Specifically, in operation, rotation of outer tube 252b results in rotation of outer bevel gear 252a of first gear assembly 250, which results in rotation of outer bevel gear 262a of second gear assembly 260 to rotate proximal bracket 218 of distal hub assembly 216 about first pivot axis "Y-Y" and thus pivot jaws 232, 234 about first pivot axis "Y-Y", as indicated by arrow "A".

Also in operation, when the second gear train is actuated, end effector 200 is pivoted or articulated about second pivot axis "W-W". Specifically, in operation, rotation of intermediate tube 254b results in rotation of intermediate bevel gear 254a of first gear assembly 250, which results in rotation of intermediate bevel gear 264a of second gear assembly 260, which results in rotation of intermediate proximal bevel gear 274a and distal bevel gear 274b of third gear assembly 270, which results in rotation of intermediate bevel gear 284a of fourth gear assembly 280 to rotate distal bracket 220 of distal hub assembly 216 about second pivot axis "W-W" and thus rotate jaws 232, 234 about second pivot axis "W-W", as indicated by arrow "B".

Additionally, in operation, when the third gear train is actuated, end effector 200 actuated to open/close jaws 232, 234. Specifically, in operation, rotation of inner tube 256b results in rotation of inner bevel gear 256a of first gear assembly 250, which results in rotation of inner bevel gear 266a of second gear assembly 260, which results in rotation of inner proximal bevel gear 276a and inner distal bevel gear 276b of third gear assembly 270, which results in rotation of inner bevel gear 286a of fourth gear assembly 280, which results in rotation of inner proximal bevel gear 296a and distal bevel gear 296b of fifth gear assembly 290, and which results in opposed rotations of bevel gears 232c, 234c of jaws 232, 234 about third pivot axis "Z", as indicated by arrow "C", resulting in an opening or closing of jaws 232, 234.

Figure 10:
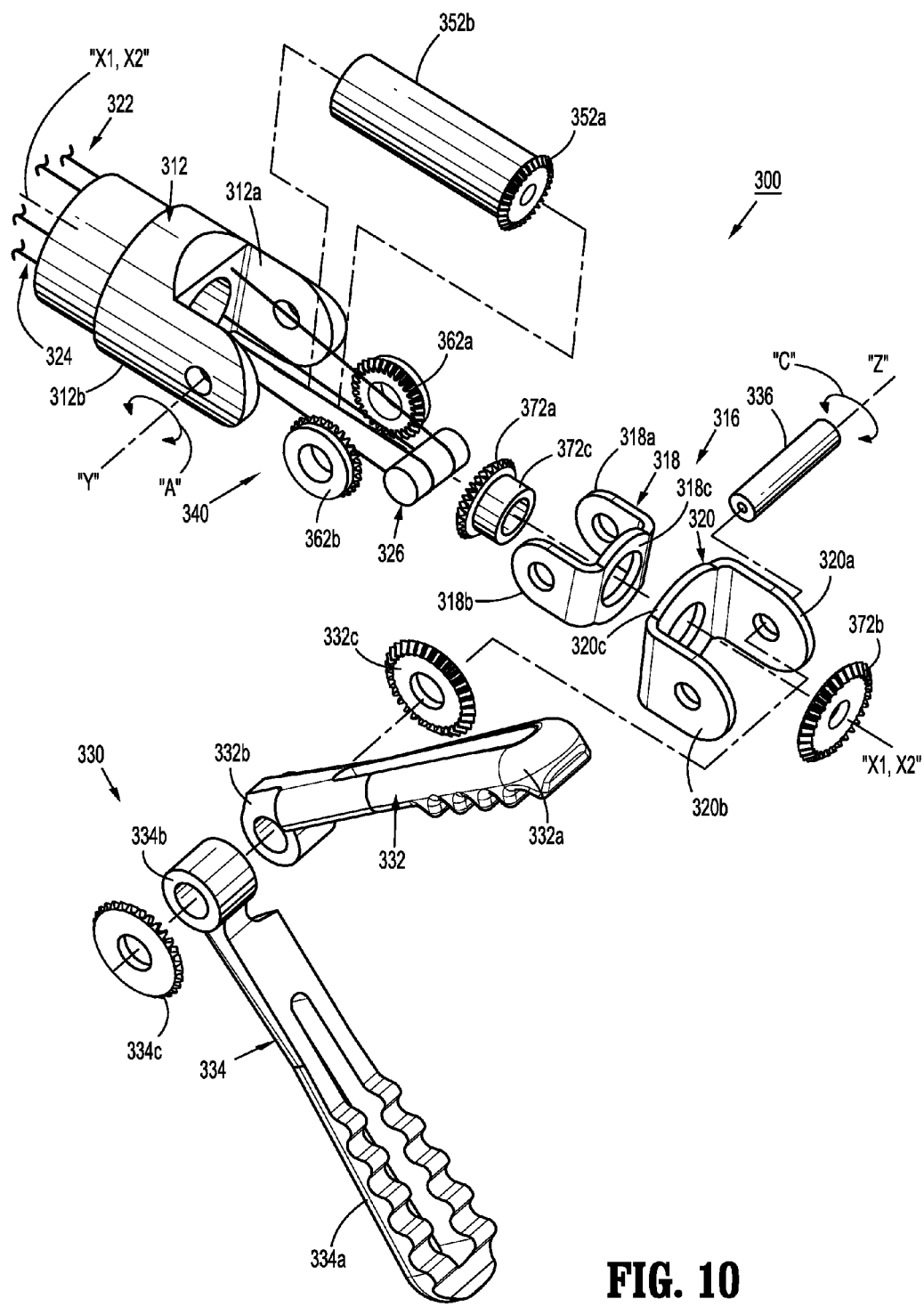
FIG. 10 is a perspective view, with parts separated, of the end effector of FIGS. 8 and 9.

Turning now to FIGS. 8-10, an end effector for connection to robot arms 2, 3 and for manipulation by control device 4, in accordance with another embodiment of the present disclosure, is generally designated as 300. End effector 300 includes a wrist assembly 310, and a jaw assembly 330 pivotally connected to wrist assembly 310. Wrist assembly 310 includes a proximal hub 312, in the form of a distally extending clevis, defining a first longitudinal axis "X1-X1." Proximal hub 312 defines a first pivot axis "Y-Y" that is oriented orthogonal to the first longitudinal axis "X1-X1." In an embodiment, first pivot axis "Y-Y" may extend through the first longitudinal axis "X1-X1." Proximal hub 312, being in the form of a clevis, includes a pair of spaced apart, opposed upright supports 312a, 312b through which first pivot axis "Y-Y" extends.

Wrist assembly 310 further includes a distal hub assembly 316 pivotally connected to upright supports 312a, 312b of proximal hub 312. Distal hub assembly 316 includes a proximal U-shaped bracket 318 having a pair of spaced apart, opposed, proximally extending, upright supports 318a, 318b interconnected by a backspan 318c. Upright supports 318a, 318b of proximal U-shaped bracket 318 are pivotally connected to respective upright supports 312a, 312b of proximal hub 312, via a pivot pin (not shown) disposed along first pivot axis "Y-Y".

Distal hub assembly 316 further includes a distal U-shaped bracket 320 having a pair of spaced apart, opposed, distally extending, upright supports 320a, 320b interconnected by a backspan 320c. Upright supports 320a, 320b of distal U-shaped bracket 320 define a second pivot axis "Z-Z" therebetween. Backspan 320c of distal U-shaped bracket 320 is pivotally connected to backspan 318c of proximal U-shaped bracket 318, about a second longitudinal axis "X2-X2." Second pivot axis "Z-Z" is oriented orthogonal to the first longitudinal axis "X1-X1."

With continued reference to FIGS. 8-10, as mentioned above, end effector 300 includes a jaw assembly 330 that is pivotally supported on a pivot pin 336 extending between upright supports 320a, 320b of distal U-shaped bracket 320 and along second pivot axis "B-B". Jaw assembly 330 includes a pair of jaws 332, 334 pivotally connected to upright supports 320a, 320b of distal U-shaped bracket 320. Specifically, each jaw 332, 334 includes a respective proximal end 332a, 334a pivotally connected to upright supports 320a, 320b of distal U-shaped bracket 320, via pivot pin 336; and a respective distal end 332b, 334b. Each distal end 332b, 334b of the pair of jaws 332, 334 defines a grip or toothed portion in juxtaposed relation to one another.

In accordance with the present disclosure and the present embodiment, end effector 300 includes a gear system 340 configured and adapted to transfer/transmit rotational forces generated by motors (Motor 1 . . . n) of control device 4 into an articulation of wrist assembly 310 along first pivot axis "Y-Y", a rotation of jaw assembly 330 along second longitudinal axis "X2-X2", and an opening/closing of jaw assembly 330.

Gear system 340 includes a bevel gear 352a supported on a distal end of an outer drive tube 352b. Outer drive tube 352b defines a lumen therethrough having a longitudinal axis that is coaxial or parallel with the first longitudinal axis "X1-X1". A proximal end of outer drive tube 352a may be acted upon, either directly or indirectly, by a respective motor (Motor 1 . . . n) of control device 4 so as to be rotated about the longitudinal axis thereof.

Gear system 340 further includes a first bevel gear 362a rotatably supported on upright support 318a of proximal U-shaped bracket 318, and a second bevel gear 362b rotatably supported on one of upright supports 318b of proximal U-shaped bracket 318. First and second bevel gears 362a, 362b are in meshing engagement with bevel gear 352a.

Gear system 340 also includes a first bevel gear 372a keyed to or non-rotatably supported on a stem 372c extending a second bevel gear 372b, wherein stem 372c extends through backspan 320c of distal U-shaped bracket 320 and through backspan 318c of proximal U-shaped bracket 318. First and second bevel gears 372a, 372b are axially disposed along second longitudinal axis "X2-X2". First bevel gear 372a is in meshing engagement with first and second bevel gears 362a, 362b.

As illustrated in FIGS. 8-10, proximal end 332a of jaw 332 defines or non-rotatably supports a bevel gear 332c, and proximal end 334a of jaw 334 defines or non-rotatably supports a bevel gear 334c. Each bevel gear 332c, 334c is in meshing engagement with second bevel gear 372b.

In accordance with the present disclosure, a gear train is defined which includes bevel gear 352a, and first and second bevel gears 362a, 362b, first and second bevel gears 372a, 372b, and bevel gears 332c, 334c of jaws 332, 334. In operation, when the gear train of end effector 300 is actuated, end effector 300 actuated to open/close jaws 332, 334. Specifically, in operation, rotation of tube 352b results in rotation of bevel gear 352a, which results in rotation of first and second bevel gears 362a, 362b, which results in rotation of first and second bevel gears 372a, 372b, which results in opposed rotations of bevel gears 332c, 334c of jaws 332, 334 about second pivot axis "Z", as indicated by arrow "C", resulting in an opening or closing of jaws 332, 334.

While bevel gears have been shown and described for incorporation into the end effectors herein described, it is contemplated and within the scope of the present disclosure that other types of gears may be used, individually or in combination with one another, such as, for example, spur gears, crown gears, worm gears, sprockets, and the like.

With reference to FIGS. 8-10, a single first cable 322 is at least partially wrapped around a cam plate or spool 326 and secured to at least one point thereof, or that the single first cable 322 may be wrapped at least once around spool 326, in the manner of a capistan. Single first cable 322 may include proximal ends that extend through robot arm 2 or 3 and operatively associated with a respective first motor and second motor (not shown) of control device 4. While a single first cable 322 is shown and described, it is contemplated that a first pair of cables (not shown) including respective distal ends may be secured to opposed sides of spool 326, or wrapped at least 180° around spool 326 and secured thereto, and including respective proximal ends extending through robot arm 2 or 3 and operatively associated with a respective first motor and second motor (not shown) of control device 4.

A single second cable 324 is at least partially wrapped around spool 326 and secured to at least one point thereof, or that the single second cable 324 may be wrapped at least once around spool 326, in the manner of a capistan. Single second cable 324 may include proximal ends that extend through robot arm 2 or 3 and operatively associated with a respective first motor and second motor (not shown) of control device 4. While a single second cable 324 is shown and described, it is contemplated that a first pair of cables (not shown) including respective distal ends may be secured to opposed sides of spool 326, or wrapped at least 180° around spool 326 and secured thereto, and including respective proximal ends extending through robot arm 2 or 3 and operatively associated with a respective first motor and second motor (not shown) of control device 4.

Spool 326 is rotatably supported along first pivot axis "Y-Y" and between upright supports 312a, 312b of proximal hub 312.

In operation, as one proximal end of first cable 322 or second cable 324 is drawn in by a corresponding motor, an other opposite end of first cable 322 or second cable 324 is let out. In so doing, jaw assembly 330 may be pivoted about first pivot axis "Y-Y", in the direction of arrow "A".

In accordance with the present disclosure, end effectors that are compact in design, and yet may transmit relatively large forces or achieve a relatively large range of motion of pivoting and rotation, are contemplated and described. The gear trains disclosed herein enable transmission of relatively high loads, and may be accomplished with tight tolerances.

Additionally, relatively high precision of control of movement of the end effectors is achieved.

It will be understood that various modifications may be made to the embodiments disclosed herein. For example, while the cam pulleys disclosed herein have been shown and described as being connected to the proximal ends of the jaws, it is contemplated and within the scope of the present disclosure, for the cam pulley to be operatively connected with the distal portion of the jaws. Therefore, the above description should not be construed as limiting, but merely as exemplifications of various embodiments. Those skilled in the art will envision other modifications within the scope and spirit of the claims appended thereto.

What is claimed is:

1. An end effector connectable to a robot arm of a robotic surgical system and actuated by at least one motor of a control device of the robot surgical system, the end effector comprising:
    a wrist assembly including:
        a proximal hub defining a respective longitudinal axis; and
        a distal hub assembly defining a respective longitudinal axis, the distal hub assembly includes:
            a proximal bracket pivotally connected to the proximal hub; and
            a distal bracket pivotally connected to the proximal bracket, the distal bracket being rotatable relative to the proximal bracket along the longitudinal axis of the distal hub assembly; and
    a jaw assembly including a pair of jaws pivotally supported on the distal bracket, each jaw including:
        a proximal portion pivotally connected to the distal bracket; and
        a distal portion extending distally of the proximal portion thereof; and
    at least one gear train supported in the wrist assembly, wherein the at last one gear train transmits forces from the at least one motor of the control device to at least one of the proximal bracket of the wrist assembly, the distal bracket of the wrist assembly and the jaw assembly; the at least one gear train enabling at least one of:
        a pivoting of the distal hub assembly relative to the proximal hub;
        a rotation of the distal bracket relative to the proximal bracket; and
        an opening or closing of the jaw assembly.

2. The end effector according to claim 1, wherein the at least one gear train includes a first gear train comprising:
    a first gear rotatably supported in the proximal hub, the first gear of the proximal hub being in operative communication with at least one motor of the control system; and
    a first gear non-rotatably supported on the proximal bracket of the distal hub assembly, wherein the first gear of the proximal bracket defines a rotation axis that is co-axial with a pivot axis of the distal hub assembly relative to the proximal hub, wherein the first gear of the proximal bracket is in meshing engagement with the first gear of the proximal hub.

3. The end effector according to claim 2, wherein the at least one gear train includes a second gear train comprising:
    a second gear rotatably supported in the proximal hub, the second gear of the proximal hub being in operative communication with at least one motor of the control system, the first gear and the second gear of the proximal hub being concentric;
    a second gear rotatably supported in the proximal bracket of the distal hub assembly, wherein the first gear and the second gear of the proximal bracket are concentric; and
    a further second gear rotatably supported in the proximal bracket of the distal hub assembly, wherein the further second gear defines a rotation axis that is co-axial with the longitudinal axis of the distal hub assembly, the further second gear being non-rotatably supported on a stem extending from the distal bracket,
    wherein the further second gear of the proximal bracket is in meshing engagement with the second gear of the proximal bracket, and wherein the second gear of the proximal bracket is in meshing engagement with the second gear of the proximal hub.

4. The end effector according to claim 3, wherein the at least one gear train includes a third gear train comprising:
    a third gear rotatably supported in the proximal hub, the third gear of the proximal hub being in operative communication with at least one motor of the control system, the first, second and third gears of the proximal hub being concentric with one another;
    a third gear rotatably supported in the proximal bracket of the distal hub assembly, wherein the first, second and third gears of the proximal bracket are concentric with one another; and
    a further third gear rotatably supported in the proximal bracket of the distal hub assembly, wherein the further third gear is co-axial and concentric with the further second gear of the proximal bracket, the further third gear being non-rotatably supported on a stem extending from a gear rotatably supported in the distal bracket,
    wherein the further third gear of the proximal bracket is in meshing engagement with the third gear of the proximal bracket, and wherein the third gear of the proximal bracket is in meshing engagement with the third gear of the proximal hub.

5. The end effector according to claim 4, wherein the at least one gear train includes a gear rotatably supported in the distal bracket of the distal hub assembly, the gear of the distal bracket being keyed to the further third gear of the proximal bracket, and wherein the proximal portion of each jaw is in meshing engagement with the gear of the distal bracket.

6. The end effector according to claim 4, wherein the first gear that is rotatably supported in the proximal hub defines a first diameter; wherein the second gear that is rotatably supported in the proximal hub defines a second diameter smaller than the first diameter; and wherein the third gear that is rotatably supported in the proximal hub defines a third diameter that is smaller than the second diameter.

7. The end effector according to claim 4, wherein the first gear that is non-rotatably supported on the proximal bracket defines a first diameter; wherein the second gear that is rotatably supported on the proximal bracket defines a second diameter smaller than the first diameter; and wherein the third gear that is rotatably supported on the proximal bracket defines a third diameter that is smaller than the second diameter.

8. The end effector according to claim 4, wherein the further second gear that is rotatably supported on the proximal bracket defines a diameter; and wherein the further third gear that is rotatably supported in the proximal bracket defines a diameter that is smaller than the diameter of the further second gear.

9. The end effector according to claim 7, wherein the proximal bracket is U-shaped including a pair of spaced apart upright supports extending in a proximal direction that are interconnected by a backspan, and wherein the first gear that is non-rotatably supported on the proximal bracket and the second and third gears that are rotatably supported on the proximal bracket are supported on one of the proximally extending upright supports of the proximal bracket.

10. The end effector according to claim 9, wherein the further second gear and the further third gear, that are rotatably supported on the proximal bracket, are supported on the backspan of the proximal bracket.

11. The end effector according to claim 4, further comprising:
   a first drive tube extending through the proximal hub and supporting the first gear on a distal end thereof, the first drive tube defining a lumen therethrough;
   a second drive tube extending through the proximal hub and through the lumen of the first drive tube, the second drive tube supporting the second gear on a distal end thereof, the second drive tube defining a lumen therethrough; and
   a third drive tube extending through the proximal hub and through the lumen of the second drive tube, the third drive tube supporting the third gear on a distal end thereof.

12. The end effector according to claim 11, wherein the first gear that is rotatably supported in the proximal hub defines a first diameter; wherein the second gear that is rotatably supported in the proximal hub defines a second diameter smaller than the first diameter; and wherein the third gear that is rotatably supported in the proximal hub defines a third diameter that is smaller than the second diameter.

13. An end effector connectable to a robot arm of a robotic surgical system, wherein the end effector is actuated by at least one motor of a control device of the robot surgical system, the end effector comprising:
   a wrist assembly including:
      a proximal hub defining a respective longitudinal axis; and
      a distal hub assembly including:
         a proximal bracket pivotally connected to the proximal hub, the proximal bracket defining a longitudinal axis, the proximal bracket being pivotable about a first pivot axis that extends transversely to the longitudinal axis of the proximal hub; and
         a distal bracket pivotally connected to the proximal bracket, the distal bracket defining a longitudinal axis, the distal bracket being pivotable about a second pivot axis that extends transversely to the longitudinal axis of the proximal hub and transversely to the first pivot axis; and
   a jaw assembly including a pair of jaws pivotally supported on the distal bracket, each jaw including:
      a proximal portion pivotally connected to the distal bracket; and
      a distal portion extending distally of the proximal portion thereof; and
   at least one gear train supported in the wrist assembly, wherein the at last one gear train transmits forces from the at least one motor of the control device to at least one of the proximal bracket of the wrist assembly, the distal bracket of the wrist assembly and the jaw assembly; the at least one gear train enabling at least one of:
      a pivoting of the proximal bracket relative to the proximal hub;
      a pivoting of the distal bracket relative to the proximal bracket; and
      an opening or closing of the jaw assembly.

14. The end effector according to claim 13, wherein the at least one gear train includes a first gear train comprising:
   a first gear rotatably supported in the proximal hub, the first gear of the proximal hub being in operative communication with at least one motor of the control system; and
   a first gear non-rotatably supported on the proximal bracket of the distal hub assembly, wherein the first gear of the proximal bracket defines a rotation axis that is co-axial with the first pivot axis, wherein the first gear of the proximal bracket is in meshing engagement with the first gear of the proximal hub.

15. The end effector according to claim 14, wherein the at least one gear train includes a second gear train comprising:
   a second gear rotatably supported in the proximal hub, the second gear of the proximal hub being in operative communication with at least one motor of the control system, the first gear and the second gear of the proximal hub being concentric;
   a second gear rotatably supported in the proximal bracket and along the first pivot axis, wherein the first gear and the second gear of the proximal bracket are concentric; and
   a proximal second gear rotatably supported in the proximal bracket of the distal hub assembly and along the longitudinal axis of the proximal bracket;
   a distal second gear rotatably supported in the proximal bracket of the distal hub assembly and along the longitudinal axis of the proximal bracket, wherein the proximal second gear and the distal second gear are non-rotatably supported on a common shaft; and
   a second gear non-rotatably supported on the distal bracket of the distal hub assembly, wherein the second gear of the distal bracket defines a rotation axis that is co-axial with the second pivot axis, wherein the second gear of the distal bracket is in meshing engagement with the distal second gear of the proximal hub.

16. The end effector according to claim 15, wherein the at least one gear train includes a third gear train comprising:
   a third gear rotatably supported in the proximal hub, the third gear of the proximal hub being in operative communication with at least one motor of the control system, the first, second and third gears of the proximal hub being concentric with one another;
   a proximal third gear rotatably supported in the proximal bracket of the distal hub assembly and along the longitudinal axis of the proximal bracket;
   a distal third gear rotatably supported in the proximal bracket of the distal hub assembly and along the longitudinal axis of the proximal bracket, wherein the proximal third gear and the distal third gear of the proximal bracket are non-rotatably supported on a common shaft;
   a third gear rotatably supported on the distal bracket of the distal hub assembly, wherein the third gear of the distal bracket defines a rotation axis that is co-axial with the second pivot axis, wherein the third gear of the distal bracket is in meshing engagement with the distal third gear of the proximal bracket;
   a proximal third gear rotatably supported in the distal bracket of the distal hub assembly and along the longitudinal axis of the distal bracket, the proximal third gear that is supported in the distal bracket is in meshing engagement with the third gear rotatably supported on the second pivot axis of the distal bracket; and a distal third gear rotatably supported in the distal bracket of the distal hub assembly and along the longitudinal axis of the distal bracket, wherein the proximal third gear and the distal third gear of the distal bracket are non-rotatably supported on a common shaft;

wherein the proximal portion of each jaw is in meshing engagement with the distal third gear rotatably supported in the distal bracket.

17. The end effector according to claim 16, wherein the first gear that is rotatably supported in the proximal hub defines a first diameter; wherein the second gear that is rotatably supported in the proximal hub defines a second diameter smaller than the first diameter; and wherein the third gear that is rotatably supported in the proximal hub defines a third diameter that is smaller than the second diameter.

18. The end effector according to claim 17, wherein the first gear that is non-rotatably supported on the proximal bracket defines a first diameter; wherein the second gear that is rotatably supported on the first pivot axis of the proximal bracket defines a second diameter smaller than the first diameter; and wherein the third gear that is rotatably supported on the first pivot axis of the proximal bracket defines a third diameter that is smaller than the second diameter.

19. The end effector according to claim 18, wherein the proximal second gear that is rotatably supported in the proximal bracket defines a diameter; and wherein the proximal third gear that is rotatably supported in the proximal bracket defines a diameter that is smaller than the diameter of the proximal second gear that is rotatably supported in the proximal bracket of the distal hub assembly.

20. The end effector according to claim 19, wherein the second gear that is non-rotatably supported on the distal bracket defines a diameter; and wherein the third gear that is rotatably supported on the distal bracket defines a diameter that is smaller that the diameter of the second gear that is non-rotatably supported on the distal bracket.

\* \* \* \* \*